United States Patent
Willard et al.

(10) Patent No.: US 10,028,859 B2
(45) Date of Patent: Jul. 24, 2018

(54) USER INTERFACE DEVICE PROVIDING FOR IMPROVED COOLING OF THE SKIN

(71) Applicant: KONINKLIJKE PHILIPS N.V., Eindhoven (NL)

(72) Inventors: Nicolaas Petrus Willard, Valkenswaard (NL); Cornelis Petrus Hendriks, Eindhoven (NL); Willem Potze, Geldrop (NL); Rudolf Maria Jozef Voncken, Eindhoven (NL); Sima Asvadi, Eindhoven (NL); Joyce Van Zanten, Waalre (NL); Mareike Klee, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 304 days.

(21) Appl. No.: 14/387,584

(22) PCT Filed: Mar. 8, 2013

(86) PCT No.: PCT/IB2013/051858
§ 371 (c)(1),
(2) Date: Sep. 24, 2014

(87) PCT Pub. No.: WO2013/144753
PCT Pub. Date: Oct. 3, 2013

(65) Prior Publication Data
US 2015/0040909 A1   Feb. 12, 2015

Related U.S. Application Data

(60) Provisional application No. 61/616,024, filed on Mar. 27, 2012.

(51) Int. Cl.
*A61F 7/10* (2006.01)
*A61M 16/00* (2006.01)
(Continued)

(52) U.S. Cl.
CPC ............ *A61F 7/10* (2013.01); *A61M 16/0057* (2013.01); *A61M 16/06* (2013.01);
(Continued)

(58) Field of Classification Search
CPC .............. A61M 16/06; A61M 16/0605; A61M 16/0611; A61M 16/0616; A61M 16/0622;
(Continued)

(56) References Cited

U.S. PATENT DOCUMENTS 5,438,981 A   8/1995 Starr
5,655,527 A   8/1997 Scarberry
(Continued)

FOREIGN PATENT DOCUMENTS

DE   10149908 A1   4/2003
EP   2281595 A1   2/2011
(Continued)

OTHER PUBLICATIONS

Arens E. and Zhang H., Chapter 16 "The skin's role in human thermoregulation and comfort" from "Thermal and Moisture Transport in Fibrous Materials", edited by N. Pan and P. Gibson, 2006.*
(Continued)

*Primary Examiner* — (Jackie) Tan-Uyen T Ho
*Assistant Examiner* — Joseph D Boecker
(74) *Attorney, Agent, or Firm* — Michael W. Haas

(57) ABSTRACT

A number of user interface device embodiments are disclosed that provide for increased cooling of the skin covered by the mask and/or increased flushing of gasses, including $CO_2$, from the mask.

9 Claims, 13 Drawing Sheets

(51) Int. Cl.
*A61M 16/06* (2006.01)
*A61F 7/00* (2006.01)

(52) U.S. Cl.
CPC .... *A61M 16/0605* (2014.02); *A61M 16/0616* (2014.02); *A61M 16/0622* (2014.02); *A61M 16/0633* (2014.02); *A61F 2007/0003* (2013.01); *A61F 2007/0061* (2013.01); *A61M 2016/0661* (2013.01); *A61M 2205/02* (2013.01); *A61M 2205/05* (2013.01); *A61M 2205/362* (2013.01); *A61M 2205/3606* (2013.01); *A61M 2207/00* (2013.01); *Y10T 29/49* (2015.01)

(58) Field of Classification Search
CPC .... A61M 2016/0661; A61F 2007/0061; A62B 18/003; A62B 18/006; A62B 18/045
USPC ............ 128/205.25, 206.21, 206.24, 206.28, 128/207.12, 207.13, 207.18
See application file for complete search history.

(56) References Cited

U.S. PATENT DOCUMENTS

| | | | | |
|---|---|---|---|---|
| 5,816,240 | A * | 10/1998 | Komesaroff | A61M 15/0086 128/200.14 |
| 5,819,728 | A | 10/1998 | Ritchie | |
| 5,921,239 | A * | 7/1999 | McCall | A61M 16/06 128/205.25 |
| 5,937,851 | A * | 8/1999 | Serowski | A61M 16/06 128/202.27 |
| 6,112,745 | A * | 9/2000 | Lang | A61M 16/0816 128/204.18 |
| 9,242,061 | B2 * | 1/2016 | Lockhart | A61M 16/0816 |
| 2003/0131846 | A1 * | 7/2003 | Campbell | A62B 17/04 128/201.25 |
| 2003/0164170 | A1 * | 9/2003 | Drew | A61M 16/06 128/204.18 |
| 2004/0094157 | A1 * | 5/2004 | Dantanarayana | A61B 5/0876 128/206.21 |
| 2004/0158303 | A1 * | 8/2004 | Lennox | A61F 7/0085 607/109 |
| 2004/0255947 | A1 | 12/2004 | Martin | |
| 2006/0102185 | A1 * | 5/2006 | Drew | A61M 16/0638 128/207.13 |
| 2008/0047561 | A1 * | 2/2008 | Fu | A61M 16/08 128/207.12 |
| 2008/0110464 | A1 * | 5/2008 | Davidson | A61M 16/06 128/206.26 |
| 2008/0142015 | A1 * | 6/2008 | Groll | A61M 16/0683 128/206.24 |
| 2008/0168991 | A1 | 7/2008 | Eifler | |
| 2009/0014007 | A1 * | 1/2009 | Brambilla | A61M 16/06 128/206.24 |
| 2009/0044810 | A1 * | 2/2009 | Kwok | A61M 16/06 128/206.28 |
| 2009/0050156 | A1 * | 2/2009 | Ng | A61M 16/06 128/205.24 |
| 2009/0139525 | A1 | 6/2009 | Schirm | |
| 2009/0211575 | A1 | 8/2009 | Shiue | |
| 2009/0217929 | A1 | 9/2009 | Kwok | |
| 2009/0223519 | A1 | 9/2009 | Eifler | |
| 2009/0293880 | A1 | 12/2009 | Rutan | |
| 2010/0031958 | A1 | 2/2010 | Stewart | |
| 2011/0005524 | A1 | 1/2011 | Veliss | |
| 2011/0186051 | A1 * | 8/2011 | McAuley | A61M 16/06 128/206.24 |
| 2011/0253144 | A1 * | 10/2011 | Groll | A61M 16/0683 128/206.24 |
| 2012/0285465 | A1 * | 11/2012 | Pierro | A61B 5/0836 128/206.22 |
| 2013/0199538 | A1 * | 8/2013 | Lockhart | A61M 16/0816 128/205.25 |
| 2016/0008558 | A1 * | 1/2016 | Huddart | A61M 16/06 128/205.25 |

FOREIGN PATENT DOCUMENTS

| | | |
|---|---|---|
| WO | WO2005004963 A2 | 1/2005 |
| WO | WO2008011682 A1 | 1/2008 |
| WO | WO2008021824 A2 | 2/2008 |
| WO | WO2011003130 A1 | 1/2011 |

OTHER PUBLICATIONS

Google search—cooling of skin surface (results attached).*

* cited by examiner

USER INTERFACE DEVICE PROVIDING FOR IMPROVED COOLING OF THE SKIN

CROSS-REFERENCE TO RELATED APPLICATIONS

This patent application claims the priority benefit under 35 U.S.C. § 371 of international patent application no. PCT/IB2013/051858, filed Mar. 8, 2013, which claims the priority benefit under 35 U.S.C. § 119(e) of U.S. Provisional Application No. 61/616,024 filed on Mar. 27, 2012, the contents of which are herein incorporated by reference.

FIELD OF THE INVENTION

The present invention relates to user interface devices for transporting a gas to and/or from an airway of a user, and in particular, to a user interface device including a mechanism for providing improved cooling of the skin covered by the user interface device.

DESCRIPTION OF THE RELATED ART

A variety of respiratory masks are known that have flexible seals and cover the nose, mouth, or both of a human user. The seals, which are also commonly referred to as cushions, are intended to create a seal against the user's face. Because of the sealing effect that is created, gases can be provided at a positive pressure within the mask for delivery to the airway of the user. Such seals are typically coupled to a rigid or semi-rigid shell or frame member which provides support for the mask.

The uses for such masks range from high altitude breathing, i.e., aviation applications, to mining and fire fighting applications, to various medical diagnostic and therapeutic applications. For example, such masks are used in the delivery of continuous positive airway pressure (CPAP) or variable airway pressure, such as a bi-level pressure that varies with the user's respiratory cycle or an auto-titrating pressure that varies with the monitored condition of the user. Typical pressure support therapies are provided to treat a medical disorder, such as sleep apnea syndrome, in particular, obstructive sleep apnea (OSA), or congestive heart failure. During use, such respiratory masks, also often referred to as patient interface devices, are strapped on the head of the patient in order to interface the pressure generating device (e.g., a CPAP machine) with the patient.

A requisite of such respiratory masks is that they provide an effective seal against the user's face to prevent leakage of the gas being supplied, while also providing a comfortable user/seal interface. This problem is significant because such masks are typically worn for an extended period of time. For example, in the case of respiratory masks used to provide pressure support therapies to treat medical disorders as described above, the mask is worn for several hours in bed. Such extended use can create several discomfort problems for the user, such as the formation of red marks on the user's face, skin irritation, and/or heat and moisture discomfort. These discomfort problems can lead to reduced therapy compliance by patients as they may wish to avoid wearing an uncomfortable mask.

SUMMARY OF THE INVENTION

Accordingly, it is an object of the present invention to provide a user interface device that overcomes the shortcomings of conventional user interface device. This object is achieved according by providing a number of user interface device embodiments that provide for increased cooling of the skin covered by the mask and/or increased flushing of gasses, including $CO_2$, from the mask.

In one embodiment, a user interface element is provided that includes a first orifice for receiving a first flow of gas, and one or more second orifices for letting a second flow of gas out of the user interface element, wherein the first orifice and the one or more second orifices are positioned relative to each other such that during use of the user interface element the second flow of gas: (i) flows over and cools a skin surface of the user and out of the user interface element through the one or more second orifices, and/or (ii) flushes at least 85% of any $CO_2$ present in an interior of the user interface element (from the last patient exhalation) from the user interface element through the one or more second orifices.

In one particular exemplary embodiment, a user interface device is provided that includes a cushion having a first end portion structured to sealingly engage a user's face and a second end portion opposite the first end portion, wherein the cushion defines a chamber. The user interface device also includes a shell member including a plurality of flow segments, each of the flow segments including a chamber having an inlet located at a first end of the shell member and one or more open orifices located opposite the inlet, wherein the second end portion of the cushion is coupled to the first end of the shell member such that the chamber is in fluid communication with each of the flow segments, and wherein in response to a flow of breathing gas being delivered to the user interface device through the shell member, the user interface device is structured to cause a continuous flow of gas to flow through the chamber of the cushion and through each of the flow segments from the inlet of the flow segment to the open orifice of the flow segment.

In another particular exemplary embodiment, a user interface device is provided that includes a cushion member having a contacting portion structured to engage a portion of a user's face when the user interface device is donned by the user, wherein the cushion member defines a chamber. The contacting portion includes a textured surface having a plurality of surface features defining plurality of gaps each having a height, wherein each of the heights is greater than 100 microns, and wherein in response to a flow of breathing gas being delivered to the user interface device, the user interface device is structured to cause a continuous flow of gas to flow through the chamber of the cushion member and between the cushion member and the portion of the user's face through the gaps In yet another particular exemplary embodiment, a user interface device is provided that includes a cushion having a first end portion and a second end portion opposite the first end portion, wherein the cushion defines a chamber. The user interface device also includes a spacer/liner member located adjacent to the first end portion, wherein the spacer/liner member is structured to engage a portion of a user's face when the user interface device is donned by the user, wherein the spacer/liner member is made of a porous material, wherein in response to a flow of breathing gas being delivered to the user interface device, the user interface device is structured to cause a continuous flow of gas to flow through the chamber of the cushion and between the cushion and the portion of the user's face through the spacer/liner member.

In still another particular exemplary embodiment, a method of making a user interface device for a user is provided, wherein the user interface device has a cushion member having a contacting portion structured to engage a portion of the user's face when the user interface device is donned by the user, the cushion member defining a chamber, the contacting portion including a textured surface having a plurality of surface features defining plurality of gaps each having a height. The method includes evaluating a surface roughness of the user's skin, and choosing the actual height of each of the gaps based on the evaluated surface roughness such that the effective height of each of the gaps responsive to the user interface device being donned by the user is greater than 100 microns.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
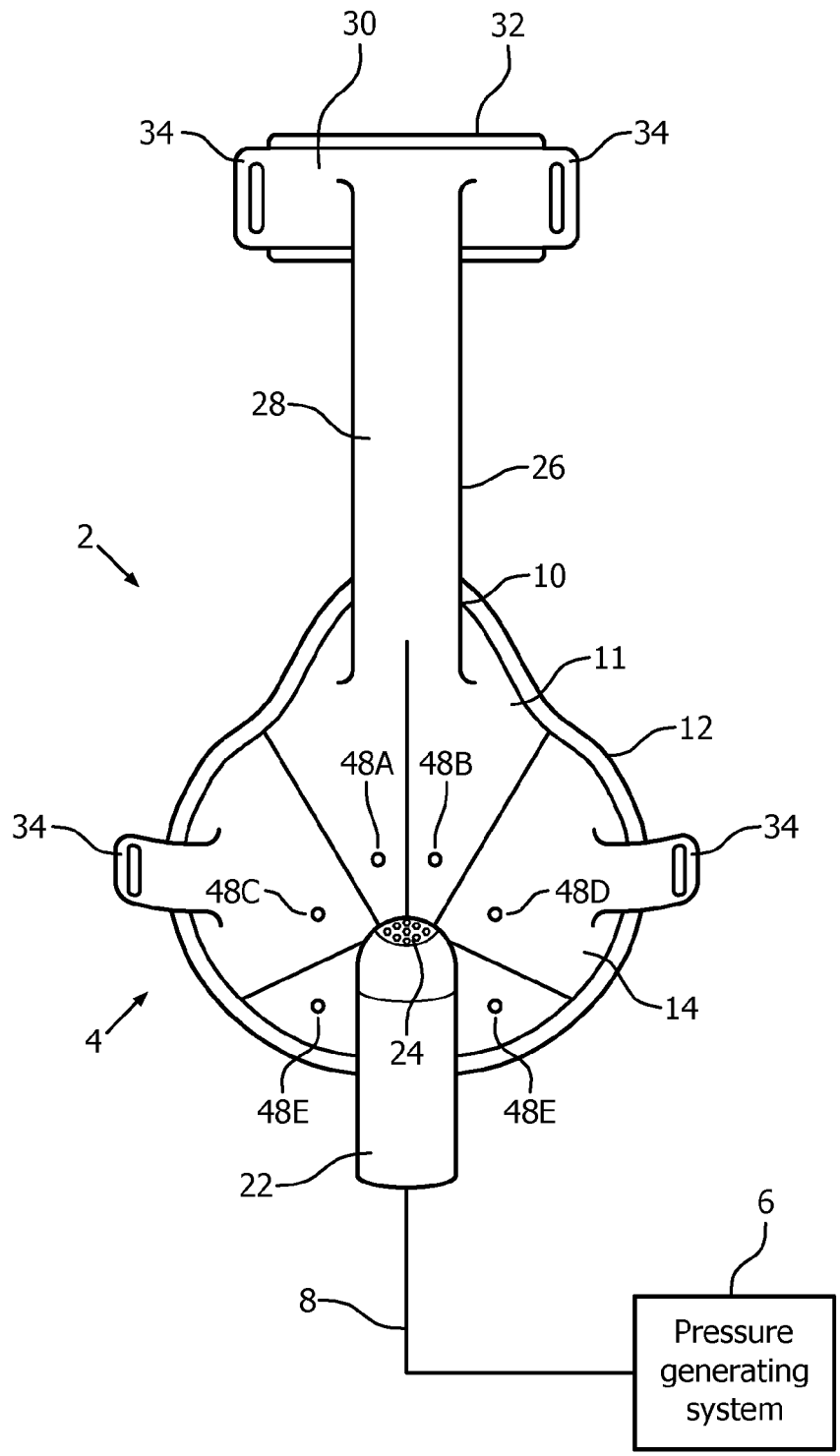
FIGS. 1 and 2 are front and side elevational views, respectively, of a system adapted to provide a regimen of respiratory therapy to a patient according to one exemplary embodiment.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the term "user interface element" shall mean a user (e.g., patient) interface device that, alone or in combination with one or more associated components, is structured to enable the delivery of a flow of breathing gas to the airways of an individual wearing the user interface element, and may include, for example and without limitation, a device that includes a cushion attached to a shell or frame member, a shell or frame member that may be coupled to a cushion, a device that includes a cushion without an associated shell or frame member, and a device that includes a cushion (with or without an associated shell or frame member) and a liner coupled to the cushion for contacting the face of the user.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Respiratory masks used to provide pressure support therapy (e.g., CPAP therapy) as described elsewhere herein have a volume of space (i.e., a chamber) that is located between the patient's face and the shell or frame member of the mask. In the prior art, for most of the time during which such a respiratory mask is used, that spatial volume is filled with the patient's exhalation gasses, which are warm and humid. It is only during inhalation that this spatial volume is flushed with air from the pressure generating device (e.g., CPAP machine) that provides the therapy breathing gas.

Thus, in the prior art, the temperature, humidity and $CO_2$ concentration inside the mask (inside the spatial volume described above) tends to be much higher than the normal values in the surrounding environment (e.g., the patient's bedroom). As a result, the skin that is covered by the mask (i.e., both the skin that is actually under and directly engaged by the mask cushion and the skin that is inside the mask but not directly covered/engaged by the mask cushion) becomes warmer and starts to sweat. However, sweating will typically not lead to any cooling as the humidity inside the mask is already very high. The increased skin temperature and humidity is uncomfortable for patients and increases the moisture level of the skin, the latter often leading to other skin problems like red marks, skin irritation, skin damage and skin wounds (e.g., pressure ulcers), particularly for the skin portions that are engaged and therefore pressed by the cushion. In addition, the higher $CO_2$ concentration is not beneficial as it will be inhaled at the next breath and increase the $CO_2$ concentration in the patient's lungs. Described herein are a number of patient interface device embodiments that provide for increased cooling of the skin covered by the mask and/or increased flushing of gasses, including $CO_2$, from the mask.

Figure 2:
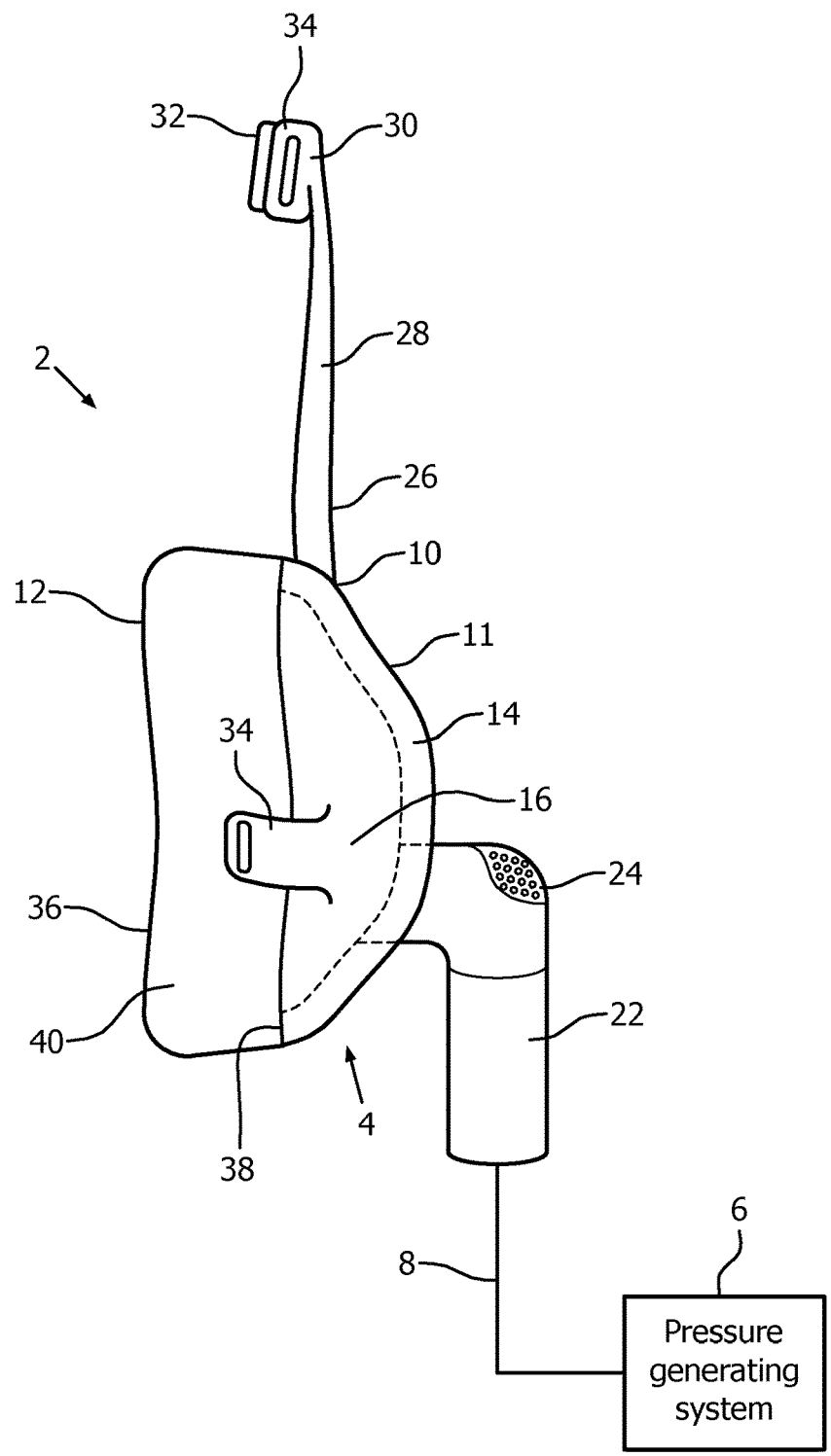

FIGS. 1 and 2 are front and side elevational views, respectively, of a system 2 adapted to provide a regimen of respiratory therapy to a patient according to one exemplary embodiment. As seen in FIGS. 1 and 2, system 2 includes a respiratory mask 4, also referred to as a patient interface device, according to one exemplary embodiment that is shown schematically attached to a pressure generating system 6 via a user circuit 8, as is conventionally known in the art. Pressure generating system 6 is any device capable of generating a flow of breathing gas or providing gas at an elevated pressure. Examples of such pressure generating systems include ventilators, constant pressure support devices (such as a continuous positive airway pressure device, or CPAP device) in which the pressure provided to the user is constant over the user's respiratory cycle, and variable pressure devices (e.g., BiPAP®, Bi-Flex®, or C-Flex™ devices manufactured and distributed by Philips Respironics of Murrysville, Pa.) in which the pressure provided to the user varies with the user's respiratory cycle, and auto-titration pressure support devices.

Figure 3:
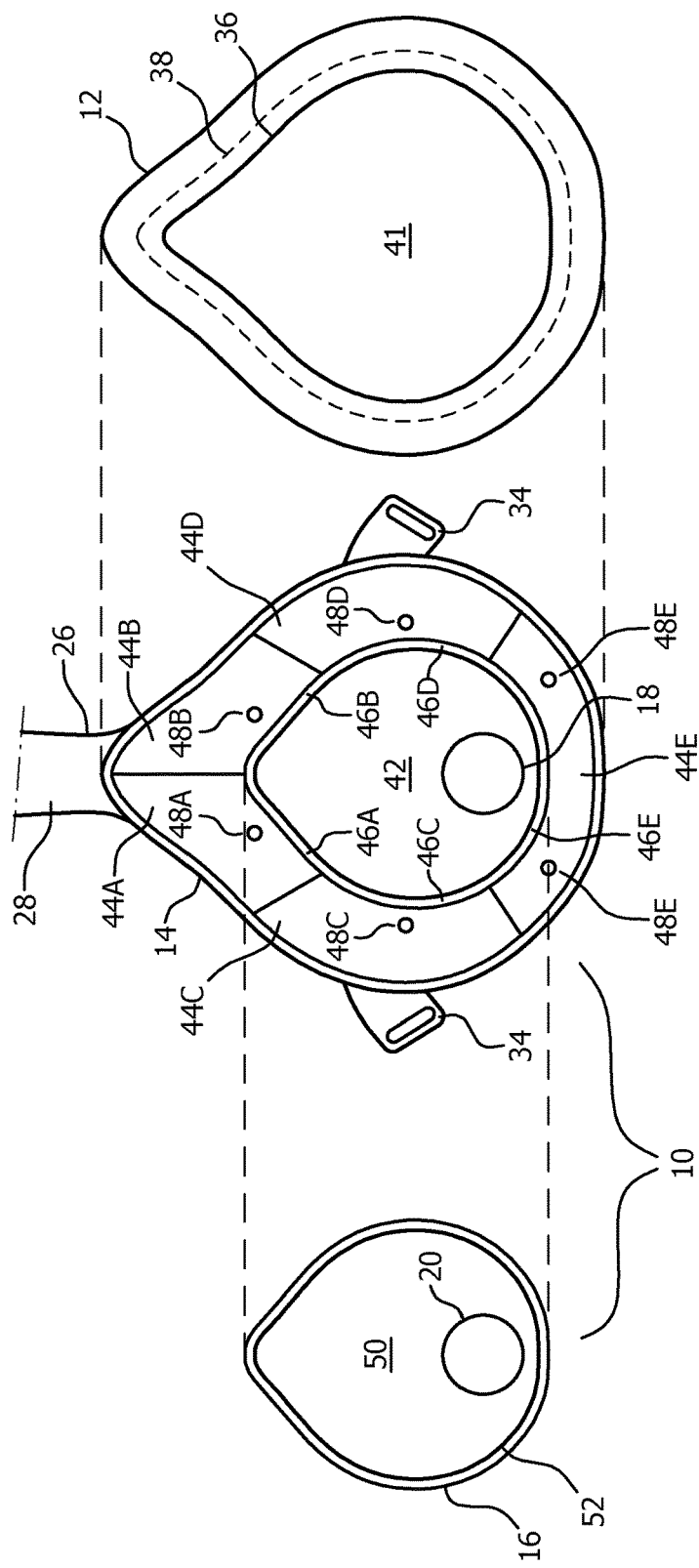
FIG. 3 is an exploded view of the respiratory mask of the system of FIGS. 1 and 2.

FIG. 3 is an exploded view of respiratory mask 4. As seen in FIGS. 1-3, respiratory mask 4 includes a shell or frame assembly 10 and a cushion 12 attached to frame assembly 10 (frame assembly 10 and a cushion 12 may be collectively referred to as a flow delivery assembly/element). Frame assembly 10 includes a faceplate portion 11 having a segmented outer shell member 14 that receives and holds an inner shell member 16, each of which is described in greater detail elsewhere herein. User circuit 8 is coupled to ports 18 and 20 defined in outer shell member 14 and inner shell member 16, respectively, and, in the illustrated embodiment, includes an elbow connector 22 for that purpose. In the exemplary embodiment, user circuit 8 is connected to frame assembly 10 so as to pivot or rotate relative to the frame assembly 10 and may or may not be detachable therefrom. In short, any suitable coupling technique for joining user circuit 8 to frame assembly 10 is contemplated by the present invention.

In the illustrated exemplary embodiment, an exhaust vent 24 is provided in elbow connector 22 for exhausting a flow of gas from mask 4 to ambient atmosphere. Such exhaust vents are conventionally used in pressure support systems that use a single-limb, i.e., a single conduit, to communicate a flow of gas to an airway of a user. Thus, the present invention contemplates that exhaust vent 24 can be any suitable exhaust vent, and can be located not only on elbow connector 22, but alternatively on another part of respiratory mask 4, such as on frame assembly 10.

Respiratory mask 4 can have any one of a number of different configurations, shapes, and sizes. In the illustrated, exemplary embodiment, respiratory mask 4 is a nasal/oral mask structured to cover the nose and mouth of the patient. However, other types of respiratory masks, such as, without limitation, a nasal mask, a nasal cushion or a full face mask, which facilitate the delivery of the flow of breathing gas to the airway of a patient, may be substituted for respiratory mask 4 while remaining within the scope of the present invention.

Frame assembly 10, in the exemplary embodiment, is formed from a rigid or semi-rigid material, such as a polycarbonate or an injection molded thermoplastic. In addition, as seen in FIGS. 1 and 2, frame assembly 10 includes a forehead support 26. The forehead support is generally T-shaped and includes a support arm 28 which is coupled to a forehead support bracket 30. Forehead support bracket 30 includes a forehead pad 32 disposed on the user contacting side to engage the forehead of the user. It is to be understood that the present invention contemplates that forehead support 26, and its individual components, can have any one of a variety of alternative configurations. The present invention also contemplates that forehead support 26 can be eliminated entirely.

In the illustrated, exemplary embodiment, a headgear (not shown) attaches to respiratory mask 4 via headgear clips 34. Headgear clips 34 attach to straps (not shown) of the headgear, for example by inserting the straps into slots provided in headgear clips 34. In the illustrated embodiment, headgear clips 34 are attached to each side of forehead support bracket 30 and to each side of the lower portion of frame assembly 10.

Cushion 12, also referred to as a seal or sealing member, is, in the exemplary embodiment, a unitary structure made of a soft, flexible, cushiony, elastomeric material, such as, without limitation, silicone, an appropriately soft thermoplastic elastomer, a closed cell foam, or any combination of such materials. As seen in FIG. 3, cushion 12 includes a first end portion 36 (defining an orifice) structured to sealingly engage the patient's face, a second end portion 38 (defining an orifice) opposite first end portion 36 that couples to the rear of frame assembly 10, and a sidewall 40 extending between first end portion 36 and second end portion 38 such that cushion 12 defines an inner chamber 41. In the illustrated embodiment, faceplate portion 11 and cushion 12 are generally triangular-shaped and thus each include an apex region, a bottom region opposite the apex region, and first and second opposite side regions. It is to be understood that the present invention contemplates using any suitable technique for attaching second end portion 38 of cushion 12 to frame assembly 10. Such techniques may include permanently bonding cushion 12 to frame assembly 10, for example using adhesives or molding cushion 12 onto frame assembly 10, or attaching cushion 12 to frame assembly 10 using mechanical fasteners in a manner wherein cushion 12 is selectively detachable from frame assembly 10. When coupled to frame assembly 10, chamber 41 of cushion 12 receives the nose and mouth of the user when respiratory mask 4 is donned by the user so that the user's airway is in fluid communication with chamber 41.

As noted elsewhere herein, frame assembly 10 includes two parts, namely segmented outer shell member 14 and inner shell member 16. As seen in FIG. 3, outer shell member 14 includes a central chamber 42 surrounded by a plurality of flow segments 44 each comprising a chamber having an inlet 46 at a first end thereof and one or more smaller orifices 48 at a second, opposite end thereof. In the illustrated, non-limiting embodiment, outer shell member 14 includes five flow segments 44, labeled 44A-44E in the FIGS. As described in greater detail herein, flow segments 44A and 44B control flow over the left and right sides of the patient's nose, respectively, flow segments 44C and 44D control flow over the left and right cheeks of the patient, respectively, and flow segment 44E controls flow over the chin of the patient.

Figure 4:
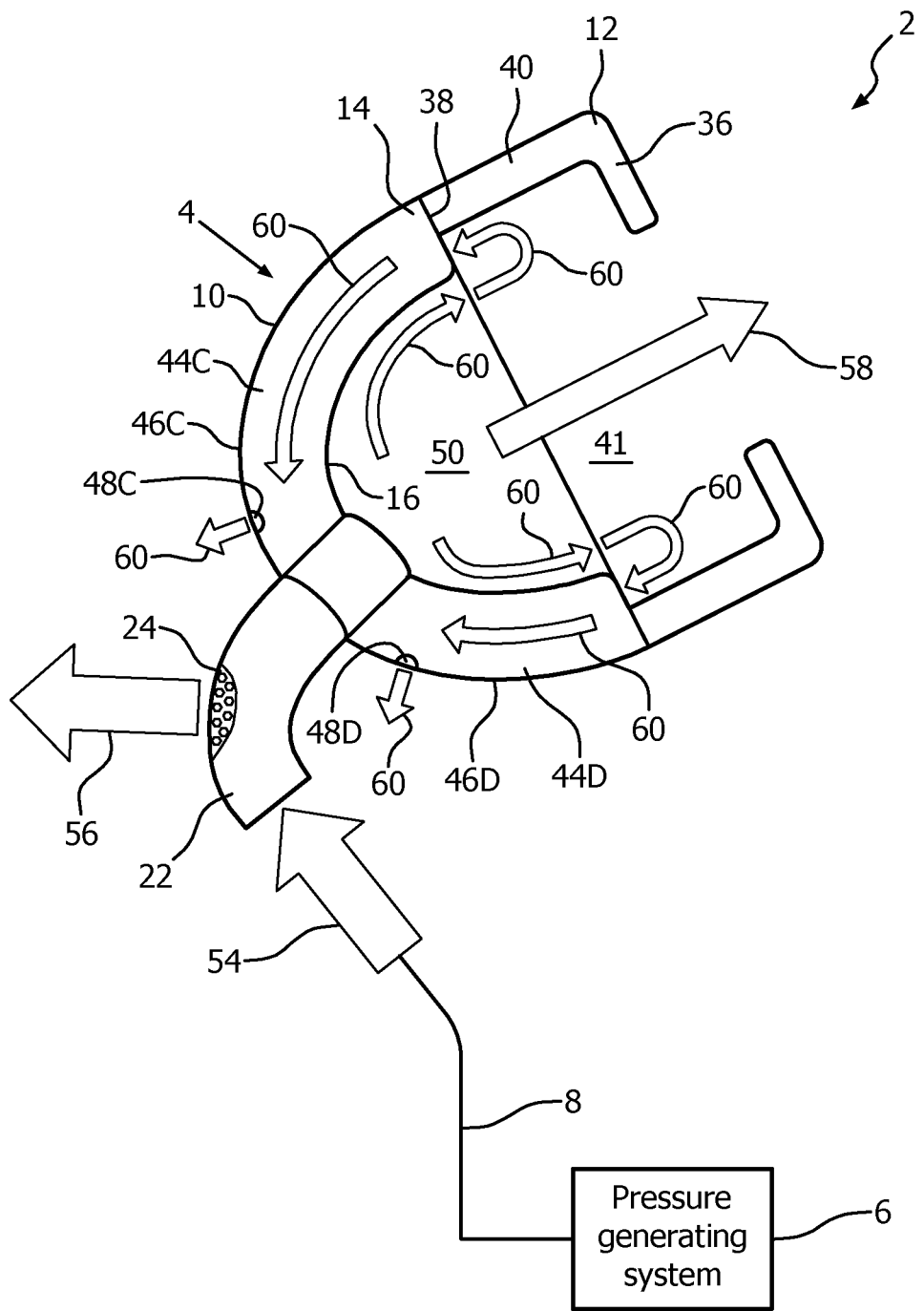
FIG. 4 is a schematic diagram of the system of FIGS. 1 and 2 showing a partial cross-sectional view of the respiratory mask thereof.

In addition, as seen in FIG. 3, inner shell member 16 defines a chamber 50 that extends from a first end 52 thereof to orifice 20. When respiratory mask 4 is assembled, inner shell member 16 is received and held within central chamber 42 of outer shell member 14 to form frame assembly 10. Inner shell member 16 may be held in place by any suitable means, such as an adhesive or a mechanical means such as a snap fit or friction fit. Cushion 12 is then attached to the back end of frame assembly 10. In particular, as seen in FIG. 4, which is a schematic diagram of system 2 showing a partial cross-sectional view of respiratory mask 4, cushion 12 is attached to frame assembly 10 in a manner such that that outer edge of second end portion 38 of cushion 12 is aligned with the outer edge of outer shell member 14 and only partially covers the inlet 46 of each flow segment 44. As a result, and as described in greater detail below, gasses are able to flow from inner chamber 41 of cushion 12 into and through flow segments 44.

The operation of respiratory mask 4 will now be described in connection with FIG. 4. As described elsewhere herein, during use, a flow of breathing gas, represented by arrow 54, is generated by pressure generating system 6 and delivered to elbow connector 22 (in the exemplary embodiment the flow of breathing gas is generated from air in the environment surrounding pressure generating system 6). A portion of the gas flow, represented by arrow 56, will exit respiratory mask 4 through exhaust vent 24 as an intentional leak of system 2. In addition, the remainder (non-leaked portion) of the gas flow will be delivered to inner chambers 50 and 41. That remaining flow will, as a result of the structure of respiratory mask 4 as described herein, provide two gas flow portions. A first gas flow portion, represented by arrow 58, will be the breathing gas that is delivered to the airway of the patient during the inspiratory phase of the patient (that flow is also present during the expiratory phase but the majority thereof is not delivered to the patient's airway and instead is opposed by the exhalation flow of the patient into chamber 50 and 41). A second gas flow portion, represented by arrows 60, will, according to an aspect of the exemplary embodiment of the present invention, be caused to flow within respiratory mask 4. That flow will be a continuous flow of gas (on the order of several ml/min as compared to several l/min for the flow represented by arrow 58) that will flow from chamber 50 to chamber 41 and to the skin that is inside respiratory mask 4 but not directly covered/engaged by cushion 12. Thereafter, the continuous flow of gas will flow to flow segments 44 (and through the chambers 46) and out of frame assembly 10 through orifices 48 of flow segments 44.

The flow represented by arrows 60 as just described will continuously flush the inner chambers 50 and 41 of respiratory mask 4 and as a result will minimize the $CO_2$, heat and moisture effects of exhaled breaths inside respiratory mask 4 that are described elsewhere herein. Instead, the flow represented by arrows 60 will cause the inside of respiratory mask 4 to be filled with cooler, drier air from pressure generating system 6 (as noted elsewhere herein, that air is, in the exemplary embodiment, taken from the environment surrounding pressure generating system 6 and will thus generally have the same temperature and humidity as such air). As a result, the skin that is inside respiratory mask 4 but not directly covered/engaged by cushion 12 will receive the flow of gas represented by arrows 60 and be cooled. In the exemplary embodiment, the flow of gas represented by arrows 60 is more than a negligible flow and is a predetermined percentage of an intentional (designed in) leak flow of respiratory mask 4 when the patient is not inhaling during use of respiratory mask 4, wherein the predetermined percentage is not more than a certain maximum percentage value. In one particular embodiment, the flow of gas represented by arrows 60 when the patient is not inhaling, while more than a negligible flow, is at most 10% of the intentional (designed in) leak flow (i.e., the certain maximum percentage value is 10%). In one exemplary implementation, the flow represented by arrows 60 when the patient is not inhaling is greater than or equal to 0.1% of the intentional (designed in) leak flow and less than or equal to 10% of the intentional (designed in) leak flow, while in another exemplary implementation the flow represented by arrows 60 when the patient is not inhaling is greater than or equal to 1% of the intentional (designed in) leak flow and less than or equal to 10% of the intentional (designed in) leak flow. In addition, the flow of gas represented by arrows 60 flows over at least one part of a user's face, the at least one part being chosen from the group of parts comprising: the nose bridge, the upper lip, the lower lip, the chin and/or the cheeks. In one particular embodiment, the parts include the nose bridge, the upper lip and the cheeks. In another particular embodiment, the parts include the nose bridge, the upper lip, the lower lip, and the cheeks. In still another particular embodiment, the parts include all of the nose bridge, the upper lip, the lower lip, the chin and the cheeks.

In addition, the higher $CO_2$ concentration gas, from the exhaled breath of the patient, will be flushed out of the mask by the flow of gas represented by arrows 60. In the exemplary embodiment, at least 85% of any $CO_2$ present in the interior of the mask (from the last exhalation) will be flushed out of the mask by the flow of gas represented by arrows 60. This value is based on a calculation that assumes exhaled breath contains 4% carbon dioxide, 500 ml of fresh air is inhaled for each breath, the dead volume of the mask is 100 ml and 1000 ppm $CO_2$ or less is not harmful for people. If the mask is flushed and at least 85% of all $CO_2$ in the mask from the last exhalation is removed, a safe level will be achieved. The corresponding flow depends on the breathing rate, the volume of inhaled air, the time between inhalation and exhalation and the actual dead volume of the mask filled with the patient nose and exhaled breath. Furthermore, as will be appreciated, the flow of gas represented by arrows 60 creates a gas flow away from the patient and minimizes the risk of direct and potentially uncomfortable gas flow directed toward the face of the patient.

As noted elsewhere herein, in the exemplary embodiment, respiratory mask 4 is a nasal/oral mask structured to cover the nose and mouth of the patient. Furthermore, in the exemplary embodiment, the length of a first flow path within respiratory mask 4 along which the flow of gas represented by arrows 60 flows in order to the reach the user's face will be at least a certain first minimum value, wherein that first flow path is defined as the shortest pathway measured from the axis of the inflow port of shell member 16 to which elbow connector 22 is attached and alongside shell member 16 and cushion 12 to the face of the user. Also, the length of a second flow path within respiratory mask 4 along which the flow of gas represented by arrows 60 flows from the user's face to an orifice 48 will be at least a certain second minimum value, wherein that flow path is defined as the shortest pathway measured from the face of the user alongside cushion 12 and shell member 16 to an orifice 48. In the exemplary embodiment, the length of the first flow path will be at least 4 cm (4-6 cm in one embodiment) and the length of the second flow path will be at least 4 cm (4-6 cm in one embodiment) such that the total of the first and second flow paths will be at least 8 cm (8-12 cm in one embodiment). The value for the first and second flow paths just described would also apply to a full/total face mask type patient interface device.

In addition, if respiratory mask 4 was adapted to be a nasal mask structured to cover the nose of the patient, the length of the first flow path in the exemplary embodiment will be 1.5-3 cm (2 cm in one particular embodiment) and the length of the second flow path in the exemplary embodiment will be 1.5-3 cm (2 cm in one particular embodiment) such that the total of the first and second flow paths in the exemplary embodiment will be 3-6 cm (4 cm in one particular embodiment).

Figure 5:
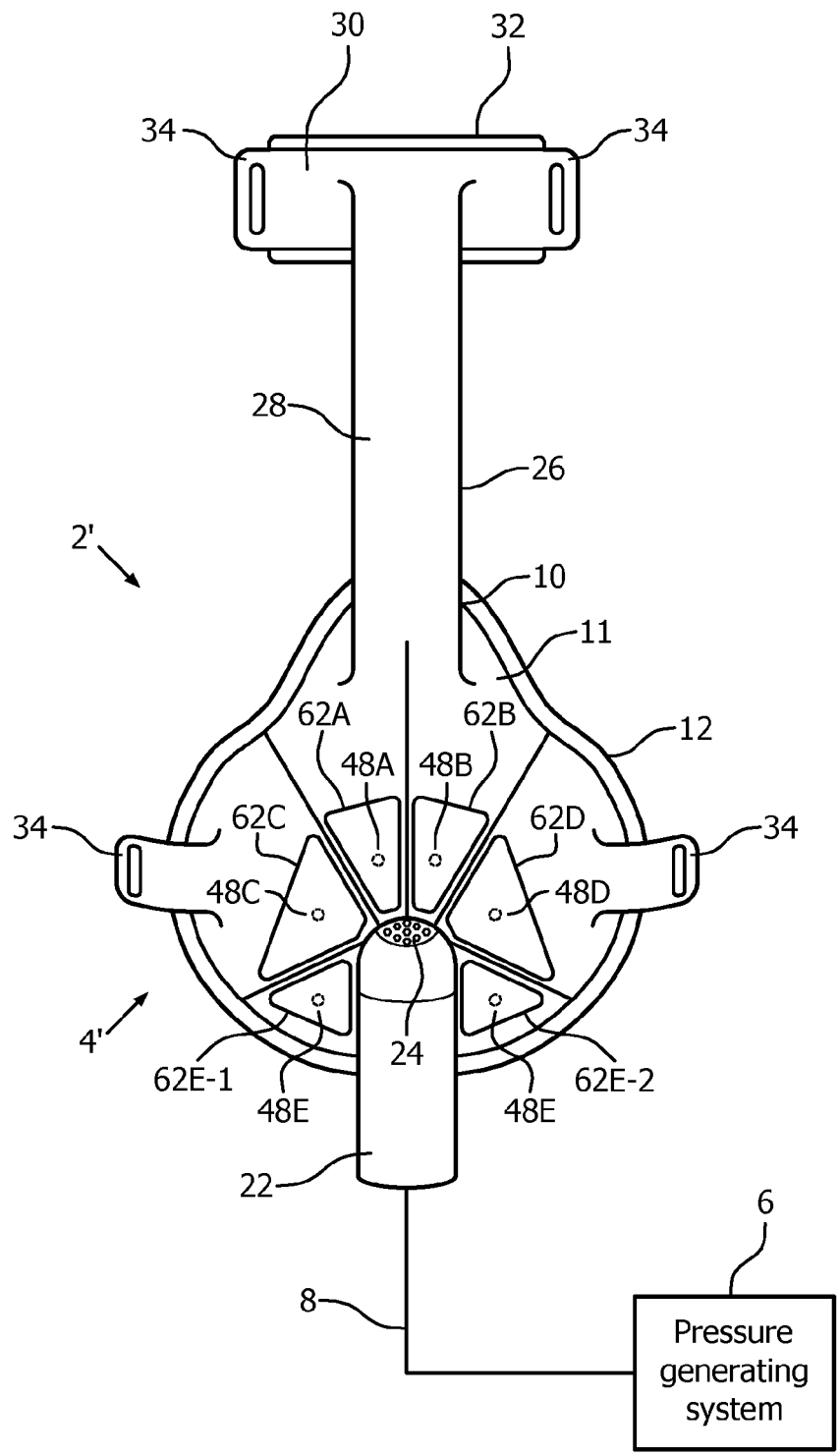
FIG. 5 is a front elevational view of a system adapted to provide a regimen of respiratory therapy to a patient according to an alternative exemplary embodiment.

FIG. 5 is a front elevational view of a system 2' adapted to provide a regimen of respiratory therapy to a patient according to an alternative exemplary embodiment. System 2' includes many of the same components as system 2 described above, and like components are labeled with like reference numerals. As seen in FIG. 5, system 2' includes alternative respiratory mask 4' having a plurality of cover members 62 that may be selectively and sealingly attached to faceplate portion 11 over orifices 48. Cover members 62 may be attached to faceplate portion 11 using, for example, and without limitation, an adhesive (e.g., an adhesive rim provided around the cover member 62), or Velcro. In another exemplary embodiment, wherein cover members 62 are made of foam (see below) or another compressible material, cover members 62 may be attached to faceplate portion 11 by compressing the cover member 62 and inserting the cover member 62 into a small pocket formed in faceplate portion 11. Once inserted, the foam cover member 62 will expand and fill the pocket creating a stable configuration. In the illustrated, exemplary embodiment, at least six cover members 62A-62E are provided for selectively covering orifices 48A-48E. Cover members 62 enable a patient to selectively control the nature/degree of the flow of gas through segmented outer shell member 14 by selectively controlling the rate of flow through each of the flow segments 44 by controlling the resistance to flow at orifices 48. In particular, cover members 62 may be made of a porous material, such as a fabric, foam, sponge, perforated foils, hairy materials like fur, high pile carpet or moleskin, or silicone rubber having a number of holes provided therein, which enables a certain degree of restricted gas flow through the associated orifice 48. Alternatively, cover members 62 may be made of a non-porous material, such as silicone rubber (or another silicone material), natural rubber, man-made rubber, cork, or an elastomer material, to prevent gas flow through the associated orifice 48 and thus completely restrict flow through the associated flow segment 44. In one particular, exemplary embodiment, one or more porous cover members 62 (e.g., having different degrees of porosity) and a non-porous cover member 62 are provided for each orifice such that the patient may, for each orifice 48, choose to leave it open/uncovered, choose to cover it with a porous cover member 62 so as to restrict flow to a certain degree (depending on the porosity of the material used to make the cover member 62), or choose to cover it with a non-porous cover member 62 so as to completely restrict flow. In this manner, the patient is able to selectively design the flow through respiratory mask 4' to suit his or her particular likes and needs. Depending on the pressure that needs to be provided to the patient by pressure generating device, the patient will be able to find a configuration that provides a comfortable skin temperature while still delivering the needed pressure. Other methods for controlling the nature/degree of the flow of gas through segmented outer shell member 14 include controlling the dimensions and/or number of the orifices 48.

Figure 6:
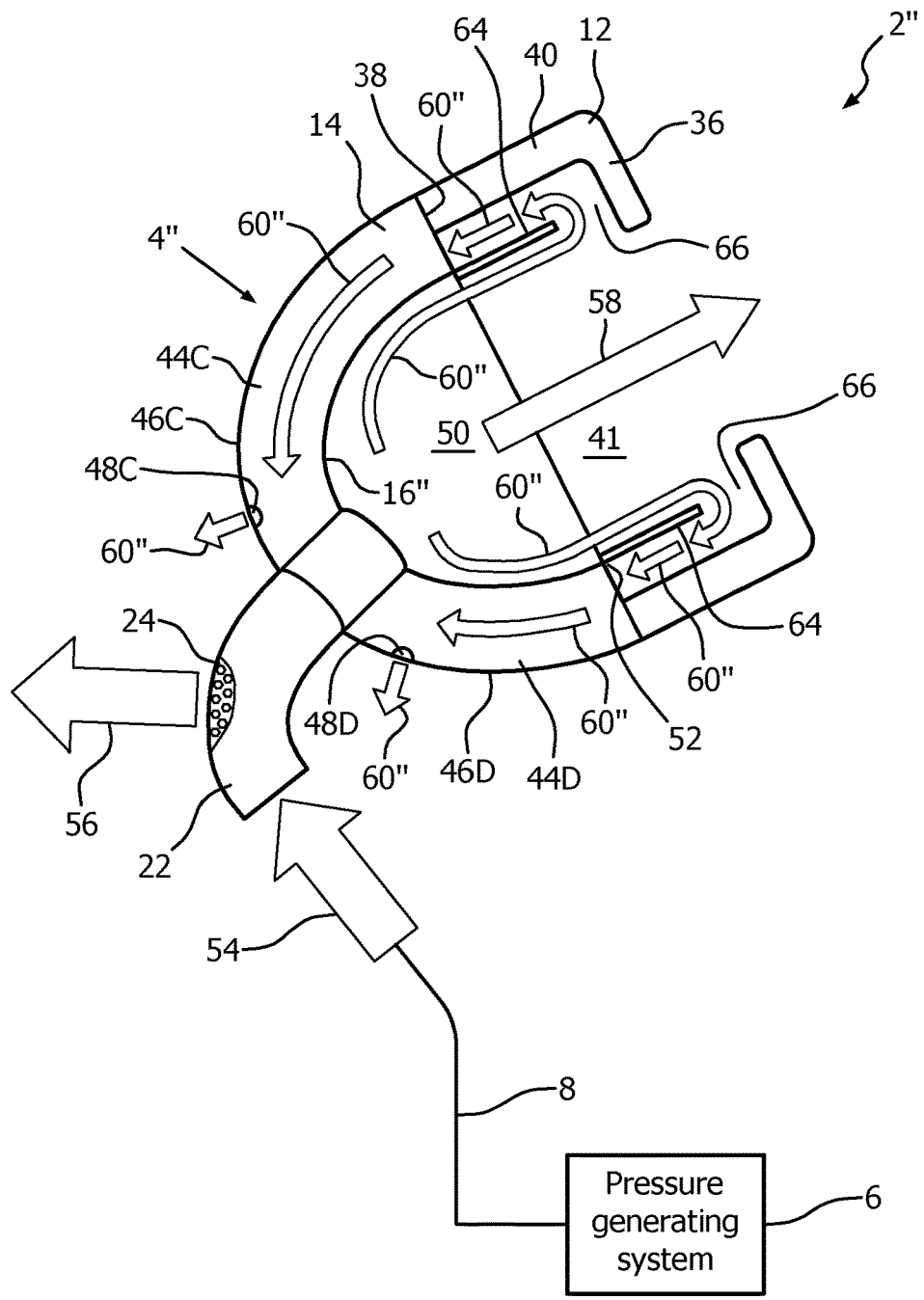
FIG. 6 is a schematic diagram in partial cross-section of a system adapted to provide a regimen of respiratory therapy to a patient according to another alternative exemplary embodiment.

FIG. 6 is a schematic diagram in partial cross-section of a system 2" adapted to provide a regimen of respiratory therapy to a patient according to a further alternative exemplary embodiment. System 2" includes many of the same components as systems 2 and 2' described above, and like components are labeled with like reference numerals. In system 2", an alternative respiratory mask 4" is provided. As seen in FIG. 6, respiratory mask 4" includes an inner shell member 16" having an extension member 64 extending from the first end 52 of inner shell member 16" into inner chamber 41 of cushion 12. In the exemplary embodiment, extension member 64 follows the contours of respiratory mask 4", and in particular the outer contours of cushion 12. As seen in FIG. 6, and entry channel 66 is formed between the distal end of extension member 64 first end portion 36 of cushion 12. The configuration of this embodiment will produce a flow represented by arrows 60". As seen in FIG. 6, that flow will contact more of the inner surface of cushion 12, and in particular, more of sidewall 40 of cushion 12, as compared to flow 60 shown in FIG. 4.

Figure 7A:
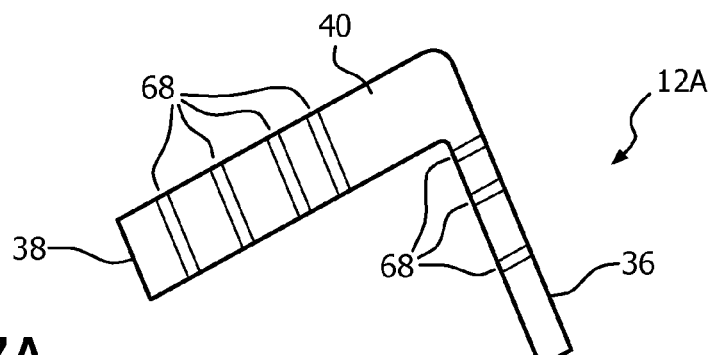
FIGS. 7A-7D are schematic representations alternative exemplary cushions that may be employed in the respiratory masks described herein.

FIG. 7A is a schematic representation of a portion of a cushion 12A according to an alternative exemplary embodiment that may be employed in respiratory mask 4, respiratory mask 4', or respiratory mask 4" as described herein. As seen in FIG. 7A, cushion 12A is perforated with a number of small channels 68 that extend through the walls of cushion 12A. As the gas flow though cushion member 12A is provided in the manner described elsewhere herein, the gas will flow through cushion 12A and cool cushion 12A. In the exemplary embodiment, channels 68 are small enough to minimize the potential for discomfort to the patient that may result from gas flowing through channels 68 and directly onto the skin. In one particular embodiment, the diameter of channels 68 is between 0.1 mm and 5 mm, and in another particular embodiment, the diameter of channels 68 is between 0.1 mm and 1 mm. Also, in the exemplary embodiment, the size and number of channels 68 is controlled so as to avoid making cushion 12A too flexible (i.e., potentially unstable). The optimal size and number of channels 68 will be determined by each particular application, and can lead appropriately flexible/stable and cool mask.

Figure 7B:
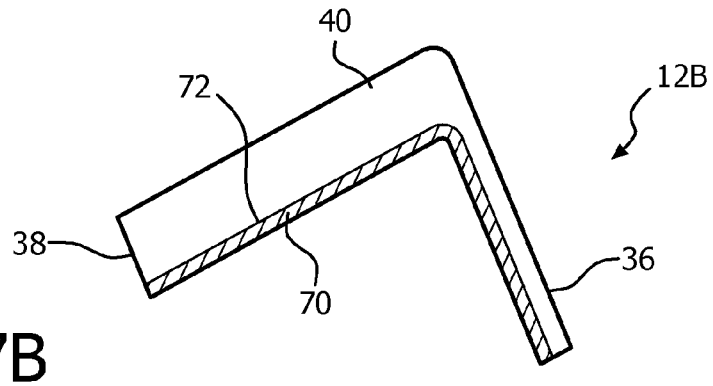

FIG. 7B is a schematic representation of a portion of a cushion 12B according to a further alternative exemplary embodiment that may be employed in respiratory mask 4, respiratory mask 4', or respiratory mask 4" as described herein. As seen in FIG. 7B, cushion 12B includes a layer 70 of material having a high specific heat conductivity that is provided on the inner surface 72 of cushion 12B. In the exemplary embodiment, layer 70 is a relatively thin layer of material, having a thickness of 20 nm-1 mm in one particular embodiment, or, alternatively, 20 nm-100 nm in another particular embodiment. Layer 70 will provide a substantially uniform temperature along inner surface 72 (by helping to spread the heat flow) and improve the heat exchange between the flow of gas within inner chamber 41 and cushion 12. In the exemplary embodiment, the material of layer 70 has a thermal conductivity of 50 W/mK or more. In one embodiment, layer 70 is made of a thin film/foil of material (e.g., metal), such as, without limitation, aluminum, Au, Cu, Ag, W, amorphous diamond, graphite, aluminum nitride, boron nitride, or graphene.

Figure 7C:
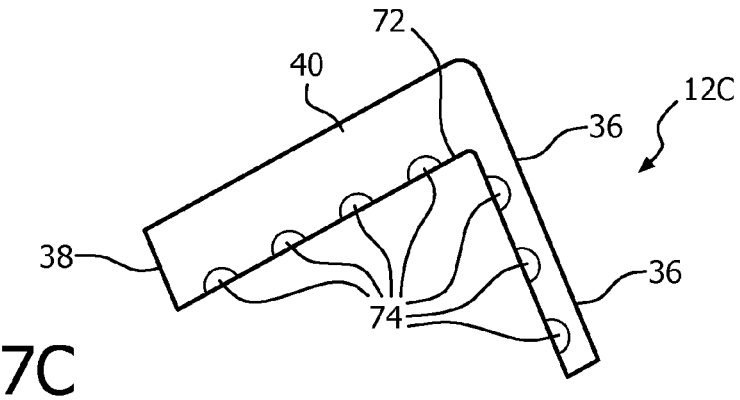

FIG. 7C is a schematic representation of a portion of a cushion 12C according to yet a further alternative exemplary embodiment that may be employed in respiratory mask 4, respiratory mask 4', or respiratory mask 4" as described herein. As seen in FIG. 7C, cushion 12C includes a varying surface texture that is provided on the inner surface 72 of cushion 12C. In the exemplary embodiment, the varying surface texture is provided by a plurality of dimples or indentations 74 that are provided in inner surface 72. In one particular implementation, dimples 74 are generally partially spherical in shape and have a diameter of between 0.1 and 5 mm. The varying surface texture of this embodiment will cause a turbulent gas flow over inner surface 72, which is a more efficient type of flow for facilitating heat exchange.

Figure 7D:
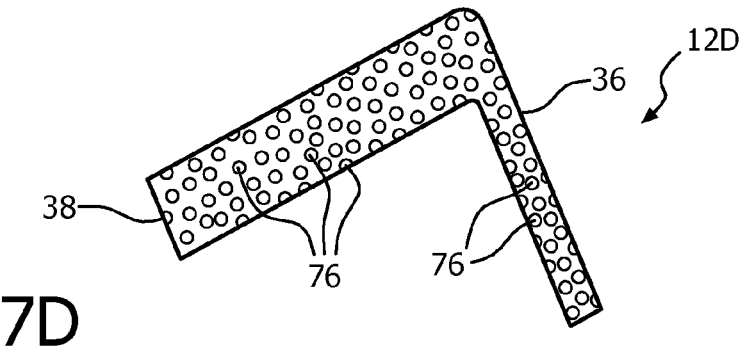

FIG. 7D is a schematic representation of a portion of a cushion 12D according to still a further alternative exemplary embodiment that may be employed in respiratory mask 4, respiratory mask 4', or respiratory mask 4" as described herein. As seen in FIG. 7D, cushion 12D includes a plurality of heat conductive particles or fibers 76 which are provided (e.g., randomly or uniformly) within the body of cushion 12D during the manufacturing thereof (e.g., a molding process) in order to increase the heat conductivity of cushion 12D so as to increase the heat flow from the patient's skin to the heat exchange area within inner chamber 41 of cushion 2. Heat conductive particles or fibers 76 may be, for example and without limitation, aluminum, tungsten, gold, copper, silver, aluminum nitride, aluminum oxide, zinc oxide, boron nitride, or carbon black particles or fibers. The optimal type and number of particles or fibers 76 will be determined by each particular application, with care being taken to not unduly increase the stiffness of cushion 12. In the exemplary embodiment, each of the particles or fibers 76 is connected to and forms a bridge (i.e., is directly or indirectly connected to) to an outside edge of cushion 12D, such as being connected to one or more other particles or fibers (i.e., the particles or fibers 76 do not all need to be connected to one another, rather at least some need to be connected and form pathways for the heat transport to an outside edge of cushion 12D; generally, the more the better, but the more that are used, the stiffer the cushion 12 will become, and care should be taken to not unduly increase the stiffness). In addition, in an alternative configuration, rather than a plurality of heat conductive particles or fibers 76, a plurality of lines of such heat conductive materials may be provided within cushion 12 extending from inner surface 72 to the outside/outer surface of cushion 12.

Figure 8:
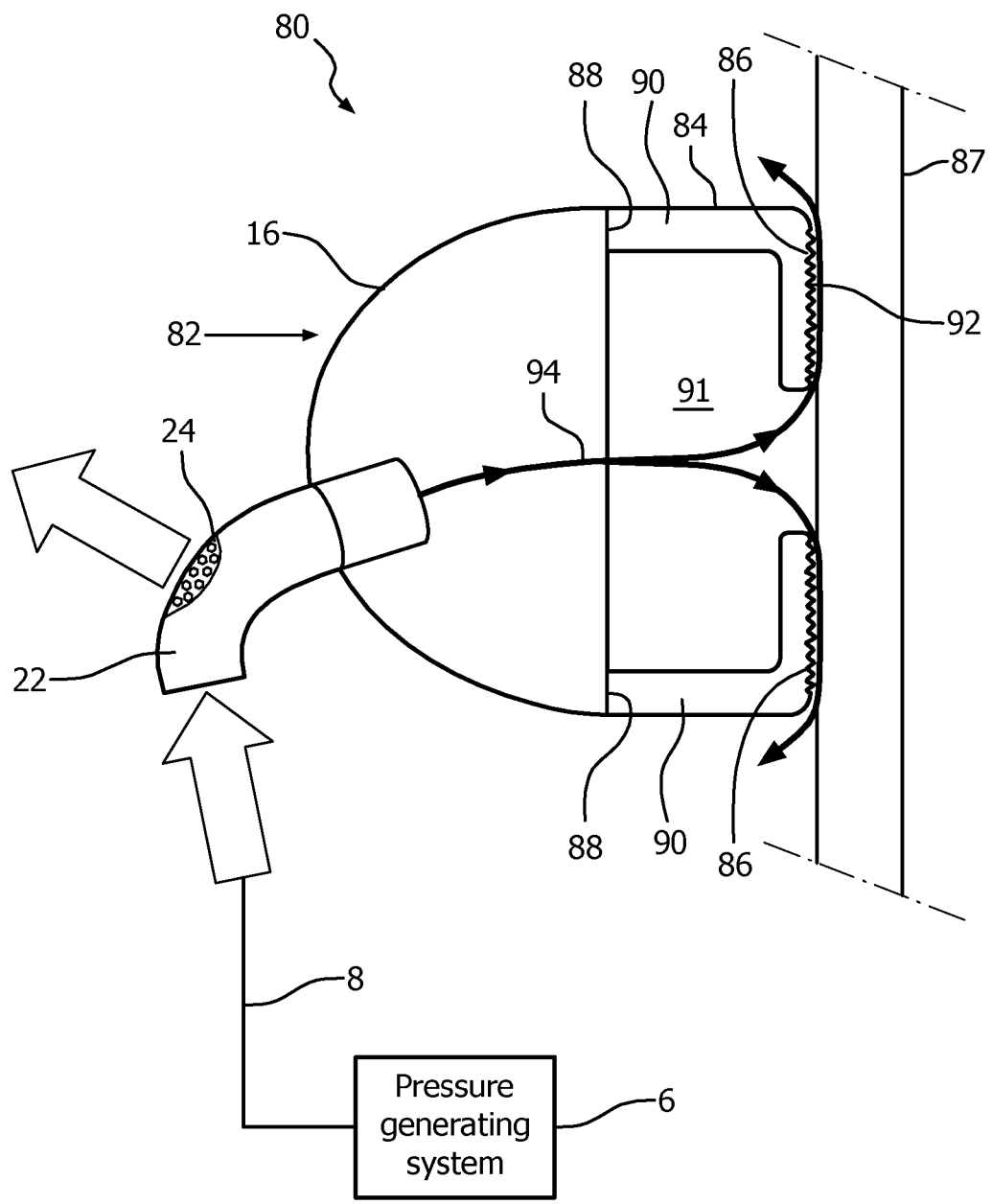
FIG. 8 is a schematic diagram in partial cross-section of a system adapted to provide a regimen of respiratory therapy to a patient according to still a further alternative exemplary embodiment.

FIG. 8 is a schematic diagram in partial cross-section of a system 80 adapted to provide a regimen of respiratory therapy to a patient according to still a further alternative exemplary embodiment. System 80 includes many of the same components as system 2 described elsewhere herein, and like components are labeled with like reference numerals. In system 80, an alternative respiratory mask 82 is provided. As seen in FIG. 8, respiratory mask 82 includes a shell member 16 as described elsewhere herein having an alternative cushion 84 attached thereto (in the exemplary embodiment, cushion 84 may be made from any of the same materials as cushion 12 described elsewhere herein). Cushion 84 includes an end portion 86 (defining an orifice) structured to engage the skin 87 of the patient's face (in the exemplary, non-limiting embodiment, end portion 86 is structured to sealingly engage the skin 87), an end portion 88 (defining an orifice for receiving gas flow into the cushion) opposite end portion 86 that couples to the rear of shell member 16, and a sidewall 90 extending between end portion 86 and end portion 88 such that cushion 12 defines an inner chamber 91. Shell member 16 and cushion 84, or cushion 84 alone, may be referred to as a flow delivery assembly/element.

End portion 86 includes a contacting portion 92 that comprises a textured surface structured to contact the skin of the user. In one embodiment, contacting portion 92 covers the entire exposed surface of end portion 86. In an alternative embodiment, contacting portion 92 covers only selected, well defined areas of end portion 86.

In one exemplary embodiment, the textured surface is a random surface having a plurality of surface features, such as, for example and without limitation, bumps, dimples, pillars, domes, valleys, ridges, undulations and serrations. In another exemplary embodiment, the textured surface is an engineered surface. As used herein, the term "engineered surface" shall mean a designed surface texture having a plurality of one or more types of surface features wherein for each type of surface feature the surface feature has a non-random, predefined/predesigned geometry and/or non-random, predefined/predesigned dimensions and/or interrelationships among one another. The surface features that may form part of an engineered surface include, for example and without limitation, bumps, dimples, pillars, domes, valleys, ridges, undulations and serrations. These surface features minimize the real area of contact with the skin, thereby providing low friction (compared to a nominally flat surface). In one particular exemplary embodiment, the surface features that may form part of an engineered surface are "non-connected surface features". As used herein, the term "non-connected surface feature" shall mean a surface feature that extends upwardly from a surface and that is not connected to any adjacent surface features at a point located above the surface from which the surface feature extends by, for example, a ridge or similar connecting structure. Examples of such "non-connected surface features" are the pillars shown in FIGS. 9C and 9D and described below.

In the embodiment of FIG. 8, the textured surface of contacting portion 92 provides well defined gaps between cushion 84 and skin 87. By providing such gaps, a small continuous gas flow as indicated by arrows 94 will be created within and through cushion 84. As seen in FIG. 8, that gas flow will flow over skin 87 and out of respiratory mask 82 through the gaps. The gas flow just described will be in direct contact with skin 87 and as a result will effectively cool skin 87, remove moisture from skin 87, and flush $CO_2$ from inner chamber 91. In the exemplary embodiment, the flow of gas represented by arrows 94 is more than a negligible flow and is a predetermined percentage of an intentional (designed in) leak flow of respiratory mask 82 when the patient is not inhaling during use of respiratory mask 82, wherein the predetermined percentage is not more than a certain maximum percentage value. In one particular embodiment, the flow of gas represented by arrows 94 when the patient is not inhaling, while more than a negligible flow, is at most 10% of the intentional (designed in) leak flow (i.e., the certain maximum percentage value is 10%). In one exemplary implementation, the flow represented by arrows 94 when the patient is not inhaling is greater than or equal to 0.1% of the intentional (designed in) leak flow and less than or equal to 10% of the intentional (designed in) leak flow, while in another exemplary implementation the flow represented by arrows 94 when the patient is not inhaling is greater than or equal to 1% of the intentional (designed in) leak flow and less than or equal to 10% of the intentional (designed in) leak flow. Also, in the exemplary embodiment, at least 85% of any $CO_2$ present in the interior of the mask 82 (from the last exhalation) will be flushed out of the mask by the flow of gas). Respiratory mask 82 will leak, but the leakage is small and the required patient pressure will still be achieved.

In addition, the flow of gas represented by arrows 94 flows over at least one part of a user's face, the at least one part being chosen from the group of parts comprising: the nose bridge, the upper lip, the lower lip, the chin and/or the cheeks. In one particular embodiment, the parts include the nose bridge, the upper lip and the cheeks. In another particular embodiment, the parts include the nose bridge, the upper lip, the lower lip, and the cheeks. In still another particular embodiment, the parts include all of the nose bridge, the upper lip, the lower lip, the chin and the cheeks.

As noted elsewhere herein, in the exemplary embodiment, respiratory mask 82 is a nasal/oral mask structured to cover the nose and mouth of the patient. Furthermore, in the exemplary embodiment, the length of the flow path within respiratory mask 82 along which the flow of gas represented by arrows 94 flows in order to the reach the user's face will be at least a certain minimum value, wherein that flow path is defined as the shortest pathway measured from the axis of the inflow port of shell member 16 to which elbow connector 22 is attached and alongside shell member 16 and cushion 90 to the face of the user (which engages the inner edge of contacting portion 92). In the exemplary embodiment, the length of the flow path will be at least 4 cm 4-6 cm in one particular embodiment). The value for the flow path just described would also apply to a full/total face mask type patient interface device. In addition, if respiratory mask 82 was adapted to be a nasal mask structured to cover the nose of the patient, the length of the flow path in the exemplary embodiment will be 1.5-3 cm (2 cm in one particular embodiment).

Figure 9A:
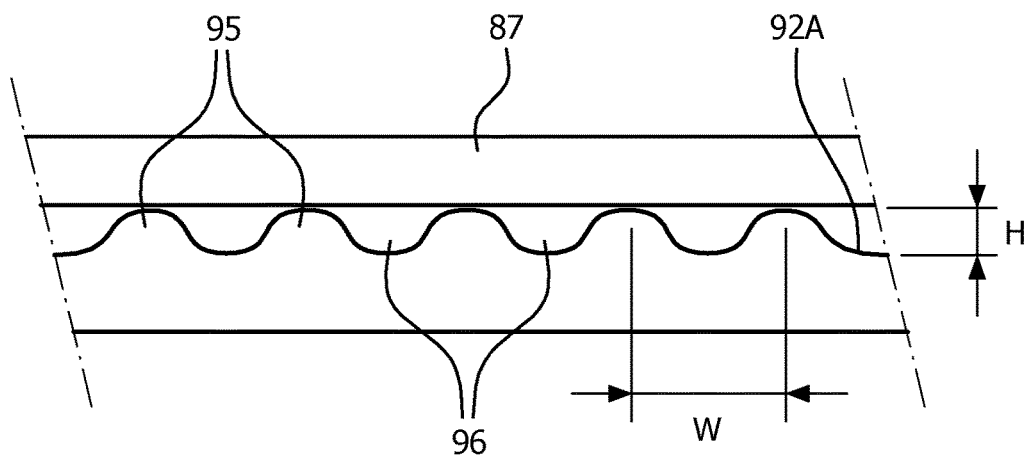
FIGS. 9A-9D are schematic representations of contacting portion of a cushion according to a number of alternative exemplary embodiments.
Figure 9B:
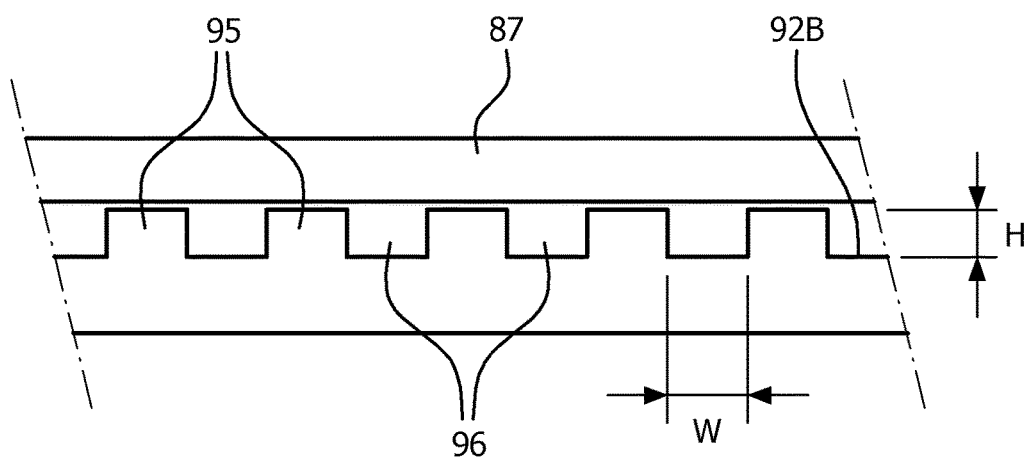
Figure 9C:
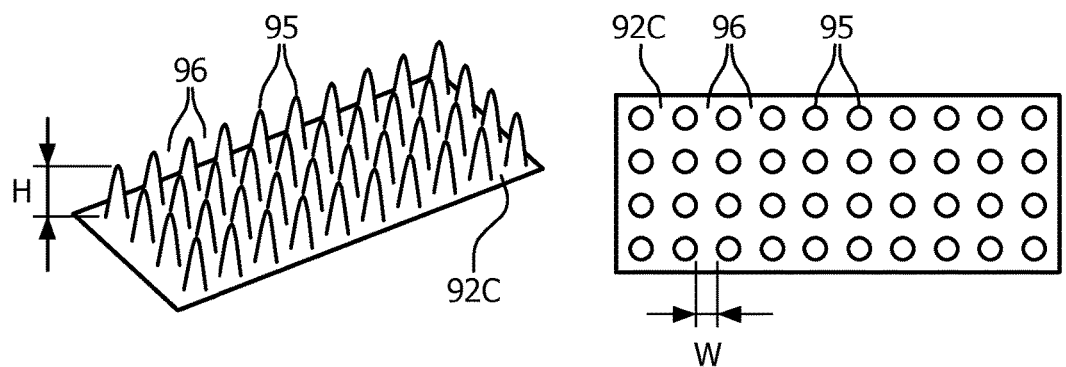
Figure 9D:
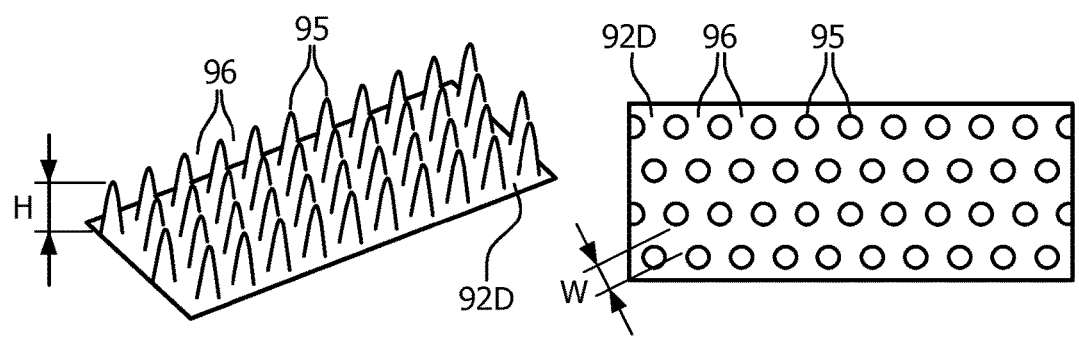

FIG. 9A is a schematic representation of contacting portion 92A according to one exemplary embodiment. As seen in FIG. 9A, contacting portion 92A comprises an engineered surface having a plurality of dome/pillar (smooth) shaped surface features, each labeled with reference numeral 95, which provide a plurality of gaps, each labeled with reference numeral 96. Each gap 96 is defined by a height H and width W. As used herein, the term "height" shall mean the vertical distance between the highest point of the tallest surface feature 95 immediately adjacent the gap 96 and the lowest surface of contacting portion 92 on which the surface features 95 sits, and the term "width" (also commonly called "pitch") shall mean the largest of the distances between highest points of adjacent surface features 95 which define the gap. As seen in FIG. 9A, the gaps 96 have equal heights H and widths W (as used herein, when comparing height and width values of gaps within a textured surface, "equal" shall mean the values are all within a 10% or less manufacturing tolerance of one another). FIGS. 9B-9D are schematic representations of contacting portions 92B-92D according to alternative exemplary embodiments. As seen in FIG. 9B-9D, contacting portion 92B comprises an engineered surface where the surface features 95 have a rectangular cross-section, and contacting portions 92C and 92D comprise engineered surfaces with different, alternative dome/pillar shaped surface features 95.

The capacity of gas flow 94 to cool skin 87 depends on the flow rate, the heat exchange efficiency, and the temperature and humidity of the gas (which, as described elsewhere herein, is in the exemplary embodiment generated from the air in the environment surrounding system 80). The flow rate in the gaps (e.g., gaps 96 in FIGS. 9A-9D) between skin 87 and cushion 84 is governed by the system pressure (e.g., CPAP pressure) and the flow resistance. The system pressure is set by the physician and cannot be changed. Thus, the only factor that may be easily controlled is the flow resistance. In the embodiment of FIG. 8, the flow resistance can be controlled by controlling the effective gap height H and/or the effective gap width W (i.e., pitch within the gap). It should be noted that the effective height of the gaps is a combination of the surface roughness of skin 87 and the roughness or texture of cushion 84. If the effective gap is too small, not enough gas (e.g., air) will flow through the gap and skin 87 will not be cooled enough. If the gaps are too large, too much gas will flow, skin 87 will become too cold and the flow will make noise that can be a nuisance for the patient. Furthermore, the heat exchange efficiency will be lower with larger gaps as only a small part of the flow will interact with skin 87.

Through testing and modeling, the present inventors have determined that, in one embodiment, effective cooling can be provided by providing a textured surface on contacting portion 92 wherein the height of the gaps formed therein are 100 microns to 1000 microns, and, in another alternative embodiment, 100 microns to 200 microns, and wherein the width/pitch of the gaps are, in one embodiment, 10 microns to 1000 microns, and in another embodiment 100 microns to 1000 microns. The present inventors have also determined that, in one particular embodiment, optimal cooling efficiency can be provided by providing a textured surface on contacting portion 92 wherein the height of the gaps formed therein are 100 microns to 150 microns. In one specific implementation, the embodiments just described may be implemented in an engineered surface wherein the heights H of the gaps are equal and are greater than 100 microns and less than or equal to 1000 microns, greater than 100 microns and less than or equal to 200 microns, or greater than 100 microns and less than or equal to 150 microns. In another specific implementation, the embodiments just described may also be implemented in a random textured surface wherein the heights H of the gaps, while not equal, are greater than 100 microns and less than or equal to 1000 microns, greater 100 microns and less than or equal to 200 microns, or greater than 100 microns and less than or equal to 150 microns.

In one particular embodiment, the gaps described herein are provided such that a controlled flow of air is created in the order of 3 g/s per cm or more in the direction of the seal that cools the skin.

Moreover, as noted above, the "effective height" of the gaps is a combination of the surface roughness of skin 87 and the roughness or texture of cushion 84. Thus, in one particular embodiment, a cushion may be custom designed for a patient wherein the surface roughness of skin 87 of the patient is taken into account. More specifically, an engineered surface may be designed for a cushion 84 wherein the heights H of the gaps are chosen such that the "effective gap height" of each gap when worn by the patient will be greater than 100 microns and less than or equal to 200 microns or, alternatively, greater than 100 microns and less than or equal to 150 microns.

In addition, as is known, with many pressure generating systems 6, the patient is able to control the humidity of the flow of gas that is generated thereby. It should be noted that the higher the humidity of the generated gas flow, the less effective the cooling will be.

Figure 10:
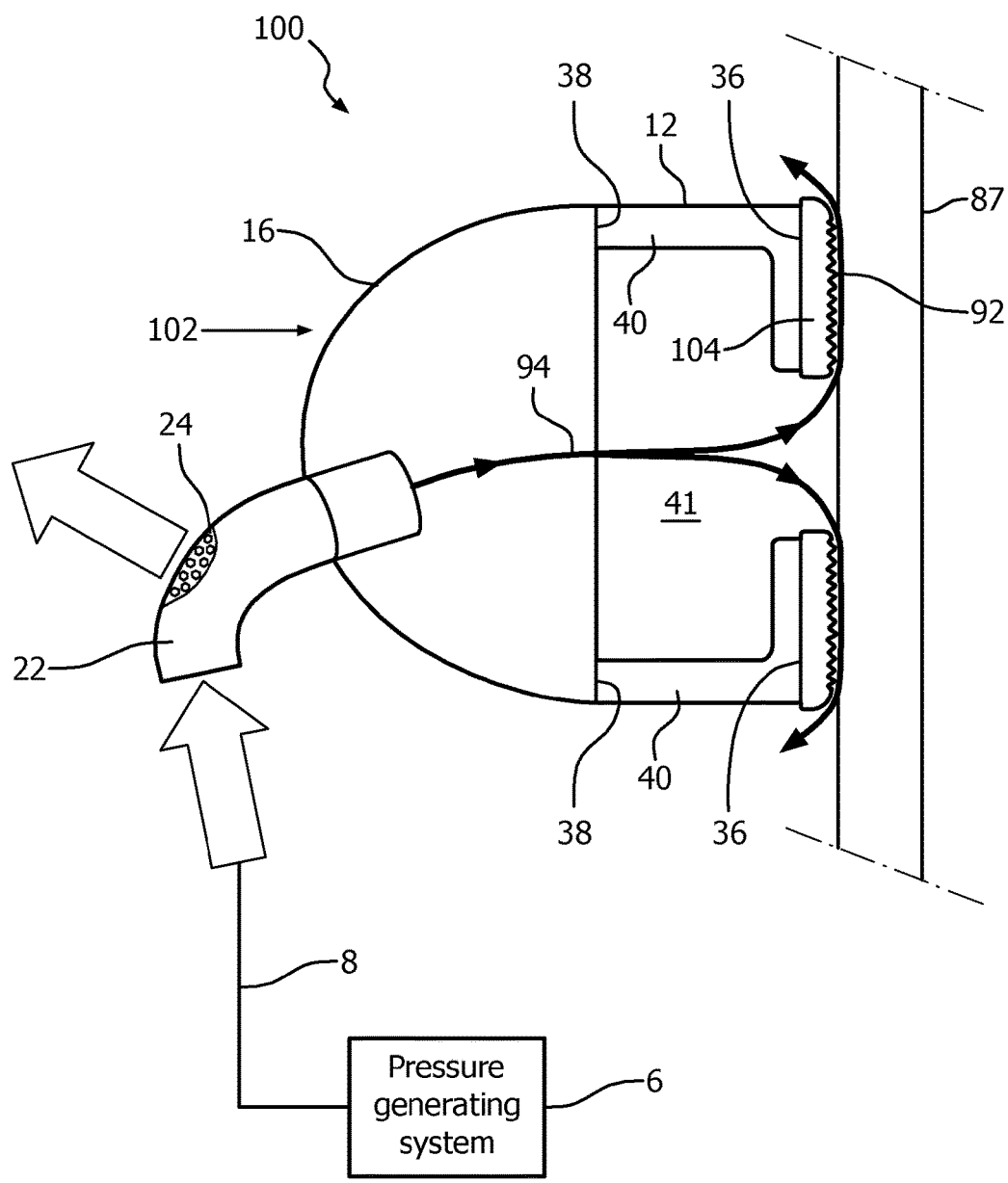
FIG. 10 is a schematic diagram in partial cross-section of a system adapted to provide a regimen of respiratory therapy to a patient according to yet a further alternative exemplary embodiment.

FIG. 10 is a schematic diagram in partial cross-section of a system 100 adapted to provide a regimen of respiratory therapy to a patient according to another alternative exemplary embodiment. System 100 includes many of the same components as systems 2 and 80 described elsewhere herein, and like components are labeled with like reference numerals. In system 100, alternative respiratory mask 102 includes a liner 104 (made of the same or a similar materials as cushion 12) that is attached (e.g., by any suitable method such as using an adhesive or molding) to end portion 36 of cushion 12. As seen in FIG. 10, liner 104 includes a contacting portion 92 having a textured surface as described elsewhere herein in connection with FIGS. 8-9D. As a result, alternative respiratory mask 102 is able to provide the same or similar continuous flow and the same or similar cooling effect as described in connection with respiratory mask 82 (see arrows 94). Shell member 16, cushion 12 and liner 104, or cushion 12 and liner 104 alone, may be referred to as a flow delivery assembly/element.

Figure 11:
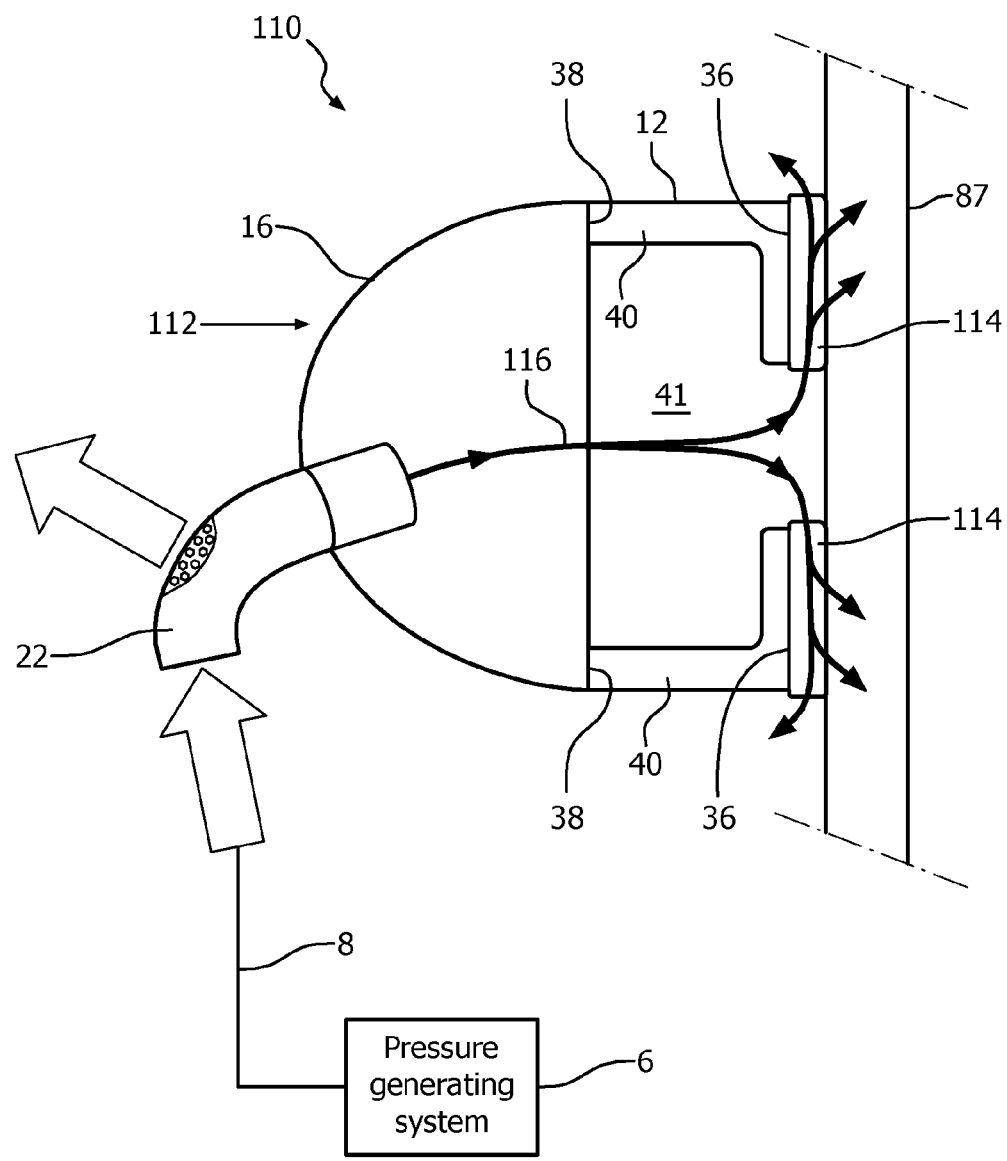
FIG. 11 is a schematic diagram in partial cross-section of a system adapted to provide a regimen of respiratory therapy to a patient according to another further alternative exemplary embodiment.

FIG. 11 is a schematic diagram in partial cross-section of a system 110 adapted to provide a regimen of respiratory therapy to a patient according to still another alternative exemplary embodiment. System 110 includes many of the same components as systems 2, 80 and 100 described elsewhere herein, and like components are labeled with like reference numerals. In system 110, alternative respiratory mask 112 includes a spacer/liner 114 that is attached (e.g., by any suitable method such as using an adhesive or molding) to first end portion 36 of cushion 12. Alternatively, spacer/liner 114 may simply rest between cushion 12 and skin 87 without being attached to cushion 12, in which case it will be held in place by the strapping forces of respiratory mask 112. In this embodiment, spacer/liner liner 114 is made of a porous material that allows a certain degree of fluid flow therethrough, as indicated by arrows 116 in FIG. 11. Liner 114 may be made of, for example and without limitation, a textile material, foam, a sponge material, fur, moleskin, high pile carpet materials. As used herein, the term "textile" shall mean a material consisting of a network of interlaced natural or artificial fibers made by, for example and without limitation, weaving, knitting, spreading, crocheting, or bonding the fibers to form the network. As a result, alternative respiratory mask 112 is able to provide a continuous gas flow and a cooling effect that is similar to that described in connection with respiratory masks 82 and 102 elsewhere herein (see arrows 116 in FIG. 11). In effect, spacer/liner 114 provides a gap for allowing fluid flow in between cushion 12 and skin 87. In one particular embodiment, the gap spacer/liner 114 is structured such that a controlled flow of air is created in the order of 3 g/s per cm or more in the direction of the seal that cools the skin. Shell member 16, cushion 12 and liner 114, or cushion 12 and liner 114 alone, may be referred to as a flow delivery assembly/element.

As noted elsewhere herein, the capacity of a gas flow through cushion 12 to cool skin 87 depends on the flow rate, the heat exchange efficiency, and the temperature and humidity of the gas (which, as described elsewhere herein, is in the exemplary embodiment generated from the air in the environment surrounding system 110). The flow rate through spacer/liner 114 is governed by the system pressure (e.g., CPAP pressure) and the flow resistance. The system pressure is set by the physician and cannot be changed. Thus, the only factor that may be easily controlled is the flow resistance. In the embodiment of FIG. 11, according to one exemplary implementation, the flow resistance can be controlled/determined by the porosity of the material used to construct spacer/liner 114. As is well known in the art, porosity is a measure of the void (i.e., "empty") spaces in a material, and is a fraction/ratio of the volume of voids ("void volume") in the material over the total/bulk volume of the material, between 0-1, or as a percentage between 0-100%. In an exemplary embodiment, weight per cubic meter is calculated by dividing weight per square meter by thickness. The specific weight of a material fabric gives the occupied volume of the solid fabric and this is recalculated to the ratio of void volume (without fabrics) to the total bulk volume. In one particular exemplary, non-limiting embodiment, the present inventors have found that effective cooling can be provided by constructing spacer/liner 114 of a material having a porosity of 80%-94%. In another particular exemplary embodiment, the porosity is 80%-90%, with one particular implementation being 88%.

However, it should be noted that care should be taken when specifying/choosing a material based on porosity. Fabrics with the same porosity can have different flow resistance. For example, one thousand thin threads can weigh as much as two big threads, but the flow resistance in the one thousand channels between the thin threads is much higher than the only channel between the two threads. Furthermore, hollow fibers have a very high porosity but can have a much smaller flow restriction. Thus, as described below, according to various other exemplary embodiments, the material for constructing spacer/liner 114 may be specified/chosen based on characteristics of the material relating to flow through the material.

As is known in the art, respiratory masks have a certain level of designed in intentional leak. In one particular exemplary embodiment, the present inventors have found that effective cooling can be provided by constructing spacer/liner 114 of a material having a certain leakage flow through the fabric expressed as a % of the intentional leak flow of the associated mask. In one exemplary implementation, the leakage flow through the fabric is 0-50% of the intentional leak flow, in another exemplary implementation, the leakage flow through the fabric is 0-10% of the intentional leak flow, and in another exemplary implementation, the leakage flow through the fabric 0-5% of the intentional leak flow. Thus, for an exemplary embodiment at 10 cmH2O having an intentional leak rate of 28 SLPM (standard liter per minute), the fabric may have a leakage flow of 1.4 SLPM (5%).

In another particular exemplary embodiment, the fabric of the spacer/liner 114 may be specified based simply on a value for the flow through the fabric at a certain pressure. In one embodiment, that flow at 10 cmH2O is 0-50 SLPM (or 5-50 SLPM), and in another embodiment, that flow at 10 cmH2O is 0-5 SLPM.

In still another particular exemplary embodiment, the fabric of the spacer/liner 114 may be specified based on the permeability of the fabric to air (with pressures ranging from 500 Pa to 2000 Pa). In one exemplary embodiment, permeability is 0-15000 $l/(m^2 \, s)$, in another exemplary embodiment, permeability is 0-1500 $l/(m^2 \, s)$, and in still another exemplary embodiment, permeability is 0-750 $l/(m^2 \, s)$. Thus, in one exemplary implementation, a mask configuration having an air permeability of 750 will yield a flow of around 4.5 liters/min through the fabric. In one particular, non-limiting embodiment, spacer/liner 114 is made from polyester fabric and contains small flexible fibers, like pillars, which will bend under any shear stress of respiratory mask 112. Skin 87 will have minimal shear stress which will lead to reduce red marks, skin irritation and even pressure ulcers for the patient.

In addition, in the exemplary embodiment, the thickness of spacer/liner 114 will be optimized to provide the most effective cooling. If spacer/liner 114 is too thick, e.g. 10 mm or more, and open, it will leak too much and even the required system (e.g., CPAP) pressure cannot be obtained. A thicker material will also have the disadvantage that a large part of the gas flow will not interact with skin 87. The heat exchange is also not efficient in this case. If spacer/liner 114 is too thin, not enough gas will flow and skin 87 will be not cooled. Furthermore, the stiffness of spacer/liner 114 is important since respiratory mask 112 is pressed onto the patient's face. If spacer/liner 114 is too soft, it will be pressed together and the effective gap becomes too small. The present inventors have found that a certain pressure applied to the skin by a mask will give red marks on the skin. In particular, the present inventors have found that the majority of people will get red marks form a mask with a pressure of 90 g. per square cm (9 kPa) or more. Thus, in one embodiment, to avoid red mark formation, the stiffness of spacer/liner 114 is selected so that it will result in a gap of at least 0.1 mm and a porosity in the range of 80-90% when a pressure is applied with a value of 10 kPa or lower.

In addition, through testing, the present inventors have determined that, in one exemplary embodiment, effective cooling will be provided by a spacer/liner 114 having a thickness between 0.1 mm and 8 mm, and in another, more particular embodiment, between 0.5 mm and 3 mm.

Furthermore, it is important to note that, in the embodiment of FIG. 11, the roughness of skin 87 has little influence on the degree of flow, and thus does not affect cooling greatly. As a result, the embodiment of FIG. 11 may be employed to provide effective cooling with a wide variety of patients with varying degrees of skin roughness.

As noted elsewhere herein, in the exemplary embodiment, respiratory mask 112 is a nasal/oral mask structured to cover the nose and mouth of the patient. Furthermore, in the exemplary embodiment, the length of the flow path within respiratory mask 112 along which the flow of gas represented by arrows 94 flows in order to the reach the user's face will be at least a certain minimum value, wherein that flow path is defined as the shortest pathway measured from the axis of the inflow port of shell member 16 to which elbow connector 22 is attached and alongside shell member 16 and cushion 12 to the face of the user (which engages the inner edge of spacer/liner 114). In the exemplary embodiment, the length of the flow path will be at least 4 cm (4-6 cm in one particular embodiment). The value for the flow path just described would also apply to a full/total face mask type patient interface device. In addition, if respiratory mask 82 was adapted to be a nasal mask structured to cover the nose of the patient, the length of the flow path in the exemplary embodiment will be 1.5-3 cm (2 cm in one particular embodiment).

In one variation of the embodiments of FIGS. 8-11, shell member 16 may be omitted, and elbow connector 22 may instead be attached directly to the orifice defined at the end portion 38, 88 of the cushion for receiving gas flow into the cushion.

Figure 12:
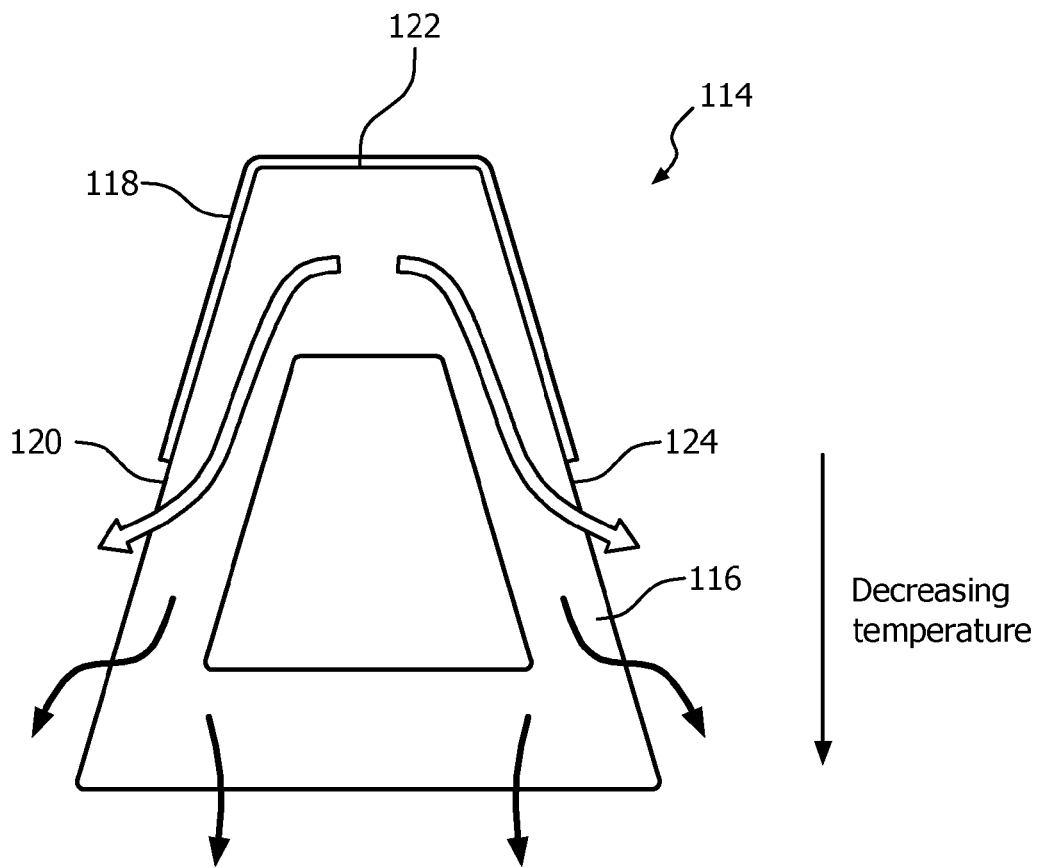
FIG. 12 is a front elevational view of spacer/liner that may be employed in the system of FIG. 11 according to one non-limiting embodiment.

FIG. 12 is a front elevational view of spacer/liner 114 according to one non-limiting embodiment. Eyes are very sensitive to any air flow and people will tend to wake up if they feel a small air flow in their eyes. Therefore, in the exemplary embodiment of FIG. 12, air flow is controlled to make sure that only the most sensitive areas of the patient are cooled and that there is minimal to no flow into the eyes of the patient. Spacer/liner 114 in this embodiment includes a porous portion 116 (made of a porous material as described elsewhere herein) and a non-porous sealing portion 118. Sealing portion 118 is made of a material such as, without limitation, silicone, liquid silicone rubber, other skin compatible resins, low porous foam, or densely woven fabrics. As seen in FIG. 12, sealing portion 118 extends from the middle of the first side 120 of spacer/liner 114, over the apex 122 of spacer/liner 114 and to the second side 124 of spacer/liner 114. Sealing portion 118 also extends over the full depth of spacer/liner 114. As a result, the sides of spacer/liner 114 near the eyes of the patient are sealed by sealing portion 118, which sealing will minimize gas flow out in the direction of the eyes of the patient. Instead, spacer/liner 114 has a flow pattern structured to guide the flow alongside to nose to the bottom side of respiratory mask 112 such that the main part of the flow through spacer/liner 114 will exit spacer/liner 114 at the chin or mouth side of respiratory mask 112, depending on whether respiratory mask 112 is a nasal mask or a nasal/oral mask.

Alternatively, the part of spacer/liner 114 that is shown as being covered by sealing portion 118 (in the neighborhood of the eyes and on the nose bridge) may instead be closed by another mechanism. For example, that area of spacer/liner 114 may be filled up with a resin, rubber, or low porosity foam, or may be made of a highly densely woven fabric. The air flow in the enclosed area will be smaller than in the non enclosed area as it has to flow a longer way than in other non enclosed area of the patch. The textile can be woven that there is a lower flow resistance in the enclosed area than in the non enclosed area. The fabric will have a lower density in the enclosed area than in the non enclosed area or it will have a higher gap height. Therefore, the amount of air flow in the enclosed area is the same as in the non enclosed area.

In addition, in the exemplary embodiment, the flow rate is different in different parts of spacer/liner 114 to optimize the comfort. This is accomplished by controlled the density or openness of the material of spacer/liner 114. In particular, flow rate is smaller near the bottom side of respiratory mask 112, as indicated by the thicker and thinner arrows. The difference in flow rate will generate areas with a different temperature, such that spacer/liner 114 will have a decreasing temperature gradient extending from top to bottom.

The effects described above in connection with FIG. 12 may also be accomplished in the embodiments that employ the textured surface for contacting the skin (FIGS. 8-10). In these embodiments, flow rate is controlled by controlling the height and/or pitch of the surface feature as described herein. For example, smaller pitch (more features per square mm) and/or smaller height may be used at the top of the surface (over the nose), and larger pitch (less features per square mm) and/or smaller height, or a random roughness with a higher Ra value (higher roughness) may be used at the bottom, of the surface (near the mouth). As a result, a textured surface may designed so as to have a decreasing temperature gradient extending from top to bottom.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A user interface element for delivering breathing gas to a user, comprising:
    a cushion having a first end portion structured to sealingly engage a face of the user and a second end portion opposite the first end portion; and a shell member coupled to the cushion, the shell member having a front end portion, a rear end portion located closer to the cushion than the front end portion, a central chamber, and a plurality of flow segment chambers surrounding the central chamber and extending from the rear end portion to the front end portion, the rear end portion having an inner edge and an outer edge spaced from the inner edge, the inner edge defining an opening of the central chamber, the front end portion having a first orifice for receiving a first flow of gas and a plurality of second orifices for letting a second flow of gas out of the user interface element, wherein each flow segment chamber includes a respective one of the second orifices and an inlet opening defined in part by a portion of the inner edge and a portion of the outer edge, wherein the second end portion of the cushion is connected to the rear end portion of the shell member in a manner wherein the second end portion of the cushion only partially covers the inlet opening of each flow segment chamber, wherein the first orifice and the second orifices are positioned relative to each other such that during use of the user interface element the second flow of gas: (i) flows over and cools a skin surface of the user and out of the user interface element through the one or more second orifices, and/or (ii) flushes at least 85% of any $CO_2$ present in an interior of the user interface element from the user interface element through the one or more second orifices.

2. The user interface element according to claim 1, wherein the second flow of gas is greater than or equal to 0.1% of an intentional leak flow of the user interface element when a user is not inhaling during use of the user interface element and less than or equal to 10% of the intentional leak flow of the user interface element when the user is not inhaling during use of the user interface element during pressure support therapy.

3. The user interface element according to claim 1, wherein the rear end portion of the shell member is coupled to the cushion such that an inner chamber of the cushion is in fluid communication with each of the flow segment chambers, and wherein in response to the first flow of gas being received through the first orifice, the user interface element is structured to cause at least a part of the second flow of gas to flow through each of the flow segment chambers from the inlet of the flow segment chamber to the second orifice of the flow segment chamber.

4. The user interface element according to claim 1, wherein the flow segment chambers include first and second flow segment chambers located in a first portion of the shell member and structured to control flow over the sides of the user's nose, third and fourth flow segment chambers located on opposite sides of a second portion of the shell member and structured to control flow over the cheeks of the user, and a fifth flow segment chamber located in a third portion of the shell member and structured to control flow over the chin of the user.

5. The user interface element according to claim 3, further comprising an inner shell member received within the central chamber, the inner shell member defining a second inner chamber in fluid communication with the inner chamber of the cushion, wherein the second inner chamber is structured to receive the flow of breathing gas and deliver the flow of breathing gas to the inner chamber of the cushion.

6. The user interface element according to claim 3, further comprising a plurality of cover members, each of the cover members being structured to be selectively attached to the shell member over a selected one of the second orifices, wherein each of the cover members is made of either a porous material that permits restricted gas flow therethrough or a non-porous material that prevents gas flow therethrough.

7. The user interface element according to claim 3, further comprising an extension member extending from the rear end portion of the shell member into the inner chamber of the cushion, the extension member being arranged for defining an entry channel in between a distal end of the extension member and a first end portion of the cushion.

8. The user interface element according to claim 3, wherein at least one of: (i) the cushion is perforated with a number channels that extend through one or more walls of the cushion, (ii) a layer of material having a thermal conductivity of 50 W/mK or more is provided on an inner surface of the cushion, wherein the layer is structured to provide a substantially uniform temperature along the inner surface, wherein the layer is at least one of: (a) a thin film of material having a thickness of 20 nm-100 nm, and (b) made form aluminum, Au, Cu, Ag, W, amorphous diamond, graphite, aluminum nitride, boron nitride, or graphene, (iii) a plurality of indentations are provided on an inner surface of the cushion to form a varying surface texture such that the varying surface texture is structured to cause a turbulent gas flow over the inner surface, and (iv) a plurality of heat conductive particles or fibers are provided within a body of the cushion.

9. A user interface element for delivering breathing gas to a user, comprising:
a cushion defining an inner chamber for receiving the breathing gas, the cushion having an inner surface facing toward the inner chamber and an outer surface facing away from the inner chamber, wherein a portion of the outer surface is structured to sealingly engage a face of the user, and wherein three or more indentations are provided on the inner surface to form a varying surface texture such that the varying surface texture is structured to cause a turbulent gas flow over the inner surface; and
a shell member coupled to the cushion, the shell member having a front end portion, a rear end portion located closer to the cushion than the front end portion, a central chamber, and a plurality of flow segment chambers surrounding the central chamber and extending from the rear end portion to the front end portion, the rear end portion having an inner edge and an outer edge spaced from the inner edge, the inner edge defining an opening of the central chamber, the front end portion having a first orifice for receiving a first flow of gas and a plurality of second orifices for letting a second flow of gas out of the user interface element, wherein each flow segment chamber includes a respective one of the second orifices and an inlet opening defined in part by a portion of the inner edge and a portion of the outer edge, wherein the first orifice and the second orifices are positioned relative to each other such that during use of the user interface element the second flow of gas: (i) flows over and cools a skin surface of the user and out of the user interface element through the one or more second orifices, and/or (ii) flushes at least 85% of any $CO_2$ present in an interior of the user interface element from the user interface element through the one or more second orifices.

* * * * *